(12) United States Patent
Scheidt et al.

(10) Patent No.: US 9,643,947 B2
(45) Date of Patent: May 9, 2017

(54) 7-MEMBERED FUSED HETEROCYCLES AND METHODS OF THEIR SYNTHESIS

(71) Applicant: Northwestern University, Evanston, IL (US)

(72) Inventors: Karl A. Scheidt, Evanston, IL (US); Javier Izquierdo Ferrer, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 14/466,677

(22) Filed: Aug. 22, 2014

(65) Prior Publication Data

US 2015/0065703 A1    Mar. 5, 2015

Related U.S. Application Data

(60) Provisional application No. 61/870,966, filed on Aug. 28, 2013.

(51) Int. Cl.
| C07D 313/06 | (2006.01) |
| C07D 313/08 | (2006.01) |
| C07D 223/16 | (2006.01) |
| C07D 223/32 | (2006.01) |

(52) U.S. Cl.
CPC ......... C07D 313/08 (2013.01); C07D 223/16 (2013.01); C07D 223/32 (2013.01)

(58) Field of Classification Search
CPC ............................ C07D 313/06; C07D 313/08
See application file for complete search history.

(56) References Cited

U.S. PATENT DOCUMENTS

| 4,857,517 A | 8/1989 | Youssefyeh et al. |
| 5,856,529 A | 1/1999 | Catt et al. |
| 2005/0079995 A1 | 4/2005 | Bedaloy et al. |
| 2011/0118231 A1 | 5/2011 | Akritopoulou-Zanze et al. |
| 2012/0238549 A1 | 9/2012 | Cusack et al. |

FOREIGN PATENT DOCUMENTS

| CN | 103027953 | 4/2013 |
| JP | 2011246419 | 12/2011 |
| WO | 2004041266 | 5/2004 |
| WO | 2005123681 | 12/2005 |
| WO | 2007010383 | 1/2007 |

(Continued)

OTHER PUBLICATIONS

Pathak, T. P. et al. J. Am. Chem. Soc. 2010, 132, 7870-7871.

(Continued)

*Primary Examiner* — Bruck Kifle
(74) *Attorney, Agent, or Firm* — Andrus Intellectual Property Law, LLP

(57) ABSTRACT

Disclosed are a new method for synthesizing 7-membered fused heterocycles and compounds synthesized by the new method. The method involves a dual activation strategy using an N-heterocyclic carbene catalyst as a first Lewis base and another second Lewis base. Compounds synthesized by the disclosed method may include new benzoxopinone compounds, as well as benzoxepane compounds and benzoazepinone compounds that optionally may be derived from the disclosed benzoxopinone compounds.

4 Claims, 11 Drawing Sheets

(56) References Cited

FOREIGN PATENT DOCUMENTS

| WO | 2007084595 | | 7/2007 |
|---|---|---|---|
| WO | WO 2009079011 | * | 6/2009 |
| WO | 2009133052 | | 11/2009 |
| WO | 2010135560 | | 11/2010 |
| WO | 2012162330 | | 11/2012 |
| WO | 2014039757 | | 3/2014 |

OTHER PUBLICATIONS

Phillips, E. M. et al.. Org. Lett. 2009, 11, 105-108.
Phillips, E. M. et al. A. Aldrichimica Acta 2009, 43, 55-66.
Pihko, P. M. Angew. Chem. Int. Ed. 2004, 43, 2062-2064.
Porter, J. H. et al. Psychopharmacol. 2009, 203, 189-191.
Qi, J. et al. Chem. Eur. J. 2013, 19, 4146-4150.
Raup, D. E. A. et al. Nat. Chem. 2010, 2, 766-771.
Rong, Z. Q. et al. Org. Lett. 2011, 13, 4080-4083.
Rueping, M. et al. Angew. Chem. Int. Ed. 2011, 50, 6706-6720.
Ryan, S. J. et al. Chem. Soc. Rev. 2013, 42, 4906-4917.
Schuetz, H. Benzodiazepines II. A Handbook.; Springer Verlag: Berlin, 1989.
Sheehan, J. C. et al. J. Am. Chem. Soc. 1966, 88, 3666-3667.
Shen, B. et al. Nature 2010, 465, 1027-U1082.
Sohn, S. S. et al. J. Am. Chem. Soc. 2004, 126, 14370-14371.
Stetter, H. Angew. Chem. Int. Ed. 1976, 15, 639-712.
Stetter, H. et al. Chem. Ber. 1979, 112, 84-94.
Taylor, M. S. et al. N. Angew. Chem. Int. Ed. 2006, 45, 1520-1543.
Terada, M. Synthesis 2010, 1929-1982.
Van de Water, R. W. et al. Tetrahedron 2002, 58, 5367-5405.
Veldhuyzen, W. F. et al. J. Am. Chem. Soc. 2003, 125, 14005-14013.
Vora, H. U. et al. Adv. Synth. Catal. 2012, 354, 1617-1639.
Wan, P. et al. Can. J. Chem. 1996, 74, 465-475.
Weinert, E. E. et al.J. Am. Chem. Soc. 2006, 128, 11940-11947.
Willis, N. J. et al. Chem. Eur. J. 2012, 18, 9160-9173.
Zhao, X. D. et al. J. Am. Chem. Soc. 2011, 133, 12466-12469.
Akiyama, T. Chem. Rev. 2007, 107, 5744-5758.
Battistuzzi, G.; Cacchi, S.; Fabrizi, G. Org. Lett. 2003, 5, 777.
Breslow, R. J. Am. Chem. Soc. 1958, 80, 3719-3726. (d) Enders, D. et al. Helv. Chim. Acta 1996, 79, 1217-1221.
Burstein, C. et al. Chem. Int. Ed. 2004, 43, 6205-6208. (b) Sohn, S. S. et al. J. Am. Chem. Soc. 2004, 126, 14370-14371. (c) Chan, A. et al. Org. Lett. 2005, 7, 905-908.
Cardinal-David, B. et al. J. Am. Chem. Soc. 2010, 132, 5345-5346.
(e) Raup, D. E. A. et al. Nat. Chem. 2010, 2, 766-771.
Chan, A. et al. Org. Lett. 2005, 7, 905-908.
Chiang, Y. et al. Pure Appl. Chem. 2000, 72, 2299-2308.
Cohen, D. T. et al. Angew. Chem. Int. Ed. 2011, 50, 1678-1682.
Cohen, D. T. et al. Chem. Sci. 2012, 3, 53-57.
Costantino, L. et al. Curr. Med. Chem. 2006, 13, 65-85.
Das, J. et al. J. Med. Chem. 1992, 35, 2610-2617.
Das, J. et al. J. Med. Chem. 1992, 35, 773-780.
Denmark, S. E. et al. Angew. Chem. Int. Ed. 2008, 47, 1560-1638.
Denmark, S. E.; et al. Acc. Chem. Res. 2000, 33, 432-440.
De Sarkar, S. et al. Chem. Eur. J. 2013, 19, 4664-4678.
Douglas, J. et al. Synthesis 2012, 2295-2309.
Doyle, A. G. et al. Chem. Rev. 2007, 107, 5713-5743.
Dugal-Tessier, J. et al. Angew. Chem. Int. Ed. 2012, 51, 4963-4967.
Enders, D. et al. Chem. Rev. 2007, 107, 5606-5655.
Enders, D. et al. Helv. Chim. Acta 1996, 79, 1217-1221.
Enders, D. et al. Helv. Chim. Acta 1996, 79, 1899-1902.
Engle, K. M.; et al. Acc. Chem. Res. 2011, 45, 788-802.
Floyd, D. M. et al. J. Med. Chem. 1992, 35, 756-772.
Floyd, D. M. et al. J. Org. Chem. 1990, 55, 5572-5579.
Grover, G. J. et al. J. Cardiovasc. Pharmacol. 1990, 16, 219-227.
Hao, L. et al. Org. Lett. 2012, 14, 2154-2157.
Izquierdo, J. et al.. Angew. Chem. Int. Ed. 2012, 51, 11686-11698.
Izquierdo, J. et al., J. Am. Chem. Soc., 2013, 135:10634-10637.
Jain, P.; et al. J. Am. Chem. Soc. 2010, 132, 11884-11886.
Jian, T. Y. et al. Org. Biomol. Chem. 2013, 11, 158-163.
Jian, T. Y. et al. Chem. Commun. 2012, 48, 10907-10909.
Kawanaka, Y. et al. J. Am. Chem. Soc. 2009, 131, 18028-18029.
Li, T. et al., J. Am. Chem. Soc., 1991, 113(20):7771-7773.
Liang, T. et al. Angew. Chem. Int. Ed. 2010, 49, 9734-9736.
Luan, Y. et al. J. Am. Chem. Soc. 2012, 134, 19965-19968.
Lv, H. et al. Adv. Syn. Catal. 2009, 351, 2882-2826.
Lv et al., Angew. Chem., Jul. 1, 2013, 52:5607-5610.
Lyons, T. W. et al. Chem. Rev. 2010, 110, 1147-1169.
Macias, F. A.; Varela, R. M.; Torres, A.; Molinillo, J. M. G. J. Nat. Prod. 1999, 62, 1636-1639.
MacMillan, D. W. C. Nature 2008, 455, 304-308.
Marion, N. et al. Angew. Chem. Int. Ed. 2007, 46, 2988-3000.
Mattson, A. E. et al. J. Am. Chem. Soc. 2007, 129, 4508-4509.
Mo, J., et al., J. Am. Chem. Soc. 2012, 134:8810-8813.
Momose, Y.; Maekawa, T.; Yamano, T.; Kawada, M.; Odaka, H.; Ikeda, H.; Sohda, T. J. Med. Chem. 2002, 45, 1518.
Mukherjee, S.; et al. Chem. Rev. 2007, 107, 5471-5569.
Nair, V. et al. Chem. Soc. Rev. 2011, 40, 5336-5346.
Noel, S. et al., Adv. Synth. Catal. 2007, 349:1129-1140.
O'Connor, S. E. et al. Fund. & Clin. Pharmacol. 1999, 13, 145-153.
Pande, P. et al. J. Am. Chem. Soc. 1999, 121, 6773-6779.
Pangborn, A. B.; Giardello, M. A.; Grubbs, R. H.; Rosen, R. K.; Timmers F. J., Organometallics 1996, 15, 1518-1520.
Asenapine definition, https://en.wikipedia.org/wiki/Asenapine, Jul. 21, 2015.
Abstract for Babu et al., "Polyphenols in madhumega chooranam, a Siddha medicine, ameliorates carbohydrate metabolism and oxidative stress in type II diabetic rats", Journal of Ethnopharmacology, Jul. 13, 2012, 142(2):331-336.
Abstract for Dreyer et al., "New insecticidal rocaglamide derivatives and related compounds from Aglaia oligophylla", J. Nat. Prod., 2001, 64(4):415-420.
Guo et al., "Two natural products, trans-phytol and (22E)-ergosta-6,9,22-triene-3beta,5alpha,8alpha-triol, inhibit the biosynthesis of estrogen in human ovarian granulosa cells by aromatase (CYP19)", Toxicology and Applied Pharmacology, 2014, 279:23-32.
Johansson et al, "Coprinol, a new antibiotic cuparane from a Coprinus species", Journal of Biosciences, 2001, 56 (112):31-34.
Abstract for Kuo et al., "Antioxidant lignans and chromone Glycosides from Eurya japonica", J. Nat. Proc., 2013, 76 (4):580-587.
Abstract for Negoro et al., "Discovery of TAK-875: A potent, selective, and orally bioavailable GPR40 agonist", ACS Med. Chem. Lett., 2010 1(6):290-294.
Abstract for Nioche et al., "Synthesis and structure-activity relationships of new ACAT inhibitors", European Journal of Medicinal Chemistry, 1995, 30(5):377-385.
Pan et al., "Bioactive flavaglines and other constituents isolated from Aglaia perviridis#", J Nat Prod., Mar. 22, 2013, 76(3):394-404.
Abstract for Peesapati et al., "Study of Friedel-Crafts acylation and Baeyer-Villiger oxidation reactions on benzocycloheptanones and 1-tetralones in acid media", J. Indian Chem. Soc., May 2009, 86:544-546.
Abstract for Pettit et al., "Antineoplastic agents, 529, isolation and structure of nootkastatins 1 and 2 from the Alaskan yellow cedar *Chamaecyparis nootkatensis*", J. Nat. Prod., 2004, 67(9):1476-1482.
Abstract for Posakony et al., "Inhibitors of Sir2: Evaluation of splitomicin analogues", J. Med. Chem., 2004, 47 (10):2635-2644.
Abstract for Rizzo et al., "In vitro, in vivo and in silico analysis of the anticancer and estrogen-like activity of guava leaf extracts", Curr Med Chem, 2014, 21(20):2322-2330.
Salim et al., "Constituents of the leaves and stem bark of Aglaia foveolata", Tetrahedron, Aug. 13, 2007, 63 (33):7926-7934.
Abstract for Shao et al., "Psiguadials A and B, two novel meroterpenoids with unusual skeletons from the leaves of Psidium guajava", Org. Lett., 2010, 12(21):5040-5043.
Abstract for Suhara et al., "Structure-activity relationship of novel menaquinone-4 analogues: modification of the side chain affects their biological activities", J. Med. Chem., 2012, 55(4):1553-1558.
Abstract for Wang et al., "Cytotoxic constituents from leaves of Aglaia elliptifolia", J. Nat. Prod., 2001, 64(1):92-94.

(56) References Cited

OTHER PUBLICATIONS

Abstract for Wang et al., "Four new cuparene-type sesquiterpenes from Flammulina velutipes", Helvetica Chimica Acta, Feb. 2012, 95(2):261-267.

Abstract for Wang et al., "Eucalyptals D and E, new cytotoxic phloroglucinols from the fruits of Eucalyptus globulus and assignment of absolute configuration", Tetrahedron Letters, May 23, 2012, 53(21):2654-2658.

Abstract for Yodsaoue et al., "Diterpenoids and triterpenoids with potential anti-inflammatory activity from the leaves of Aglaia odorata", Phytochemistry, Apr. 2012, 76:83-91.

Izquierdo, Javier, et al., "A Dual Lewis Base Activation Strategy for Enantioselective Carbene-Catalyzed Annulations", J Am Chem Soc., Jul. 24, 2013; 135(29): 10634-10637.

* cited by examiner

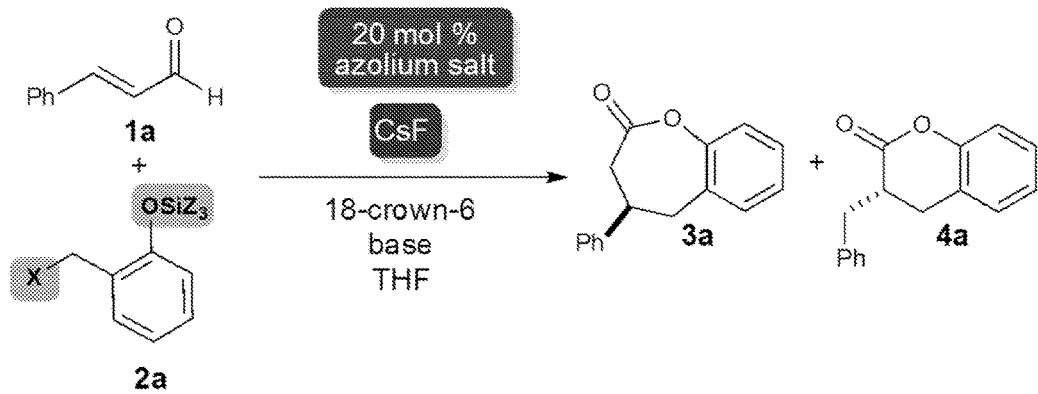
| entry | azolium | base | X / SiZ₃ | ratio (3a:4a) | yield % (er) |
|---|---|---|---|---|---|
| 1[a] | A | Cs₂CO₃ | Br / t-BuMe₂Si | 4:1 | 32 |
| 2[a] | A | CsOAc | Br / t-BuMe₂Si | 4.5:1 | 37 |
| 3[a] | B | CsOAc | Br / t-BuMe₂Si | 4:1 | 57 |
| 4[a] | C | CsOAc | Br / t-BuMe₂Si | 4.5:1 | 47 (91:09) |
| 5[a] | C | CsOAc | Cl / t-BuMe₂Si | 4.5:1 | 45 (87:13) |
| 6[a] | C | CsOAc | Br / i-Pr₃Si | 4.5:1 | 42 (89:11) |
| 7[a] | C | CsOAc | Br / Et₃Si | - | no product |
| 8[a] | C | n-Bu₄N•OAc | Br / t-BuMe₂Si | 4.5:1 | 62 (92:08) |
| 9[b] | C | n-Bu₄N•OAc | Br / t-BuMe₂Si | 5.5:1 | 64 (96:04) |
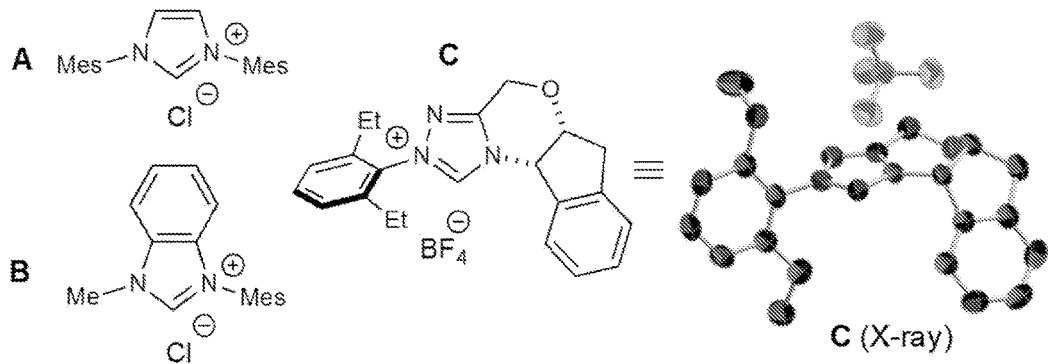
Figure 2

*Diltiazem:* Ar = *p*-OMeC$_6$H$_4$, R = OAc, X = S, Y = H
*SQ 31,486:* Ar = *p*-OMeC$_6$H$_4$, R = OAc, X = CH$_2$, Y = CF$_3$

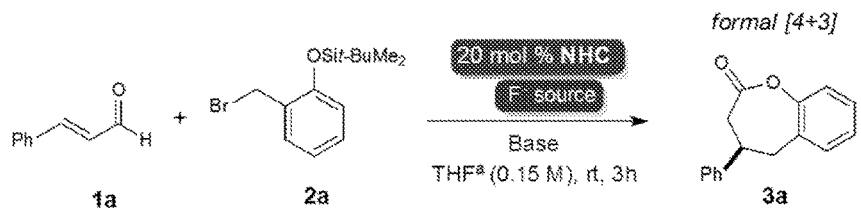

| entry | NHC | F-Source (equiv.) | Base | yield % | er |
|---|---|---|---|---|---|
| 1 | A | TBAF (2) | Cs$_2$CO$_3$ | NR | - |
| 2 | A | TMAF (2) | Cs$_2$CO$_3$ | traces | - |
| 3[b] | A | CsF (5) | Cs$_2$CO$_3$ | traces | - |
| 4 | A | CsF (5) / 18-crown-6 (4) | Cs$_2$CO$_3$ | 21 | - |
| 5 | A | CsF (2) / 18-crown-6 (2) | Cs$_2$CO$_3$ | 32 | - |
| 6 | A | CsF (2) / 18-crown-6 (2) | CsOAc | 37 | - |
| 7 | B | CsF (2) / 18-crown-6 (2) | CsOAc | 57 | - |
| 8 | D | CsF (2) / 18-crown-6 (2) | CsOAc | NR | - |
| 9 | E | CsF (2) / 18-crown-6 (2) | CsOAc | 15 | 90:10 |
| 10 | F | CsF (2) / 18-crown-6 (2) | CsOAc | 45 | 65:35 |
| 11 | G | CsF (2) / 18-crown-6 (2) | CsOAc | 38 | 63:37 |
| 12 | H | CsF (2) / 18-crown-6 (2) | CsOAc | 48 | 85:15 |
| 13 | C | CsF (2) / 18-crown-6 (2) | CsOAc | 47 | 91:09 |
| 14 | C | CsF (2) / 18-crown-6 (2) | Et$_3$N | 30 | 79:21 |
| 15 | C | CsF (2) / 18-crown-6 (2) | pyridine | 52 | 88:12 |
| 16 | C | CsF (2) / 18-crown-6 (2) | CsO$t$Bu | 25 | 81:19 |
| 17 | C | CsF (2) / 18-crown-6 (2) | Cs$_2$CO$_3$ | 43 | 85:15 |
| 18 | C | CsF (2) / 18-crown-6 (2) | 4-NO$_2$-C$_6$H$_4$COONa | 18 | 93:07 |
| 19 | C | CsF (2) / 18-crown-6 (2) | $n$-Bu$_4$N·OAc | 62 | 92:08 |
| 20[c] | C | CsF (2) / 18-crown-6 (2) | $n$-Bu$_4$N·OAc | 64 | 96:04 |

[a]Other solvents as AcOEt, CHCl$_3$ or toluene did not afford any trace of product. [b]Reaction was heated at 40 °C. [c]Reaction at criocool at −18 °C for 12h.

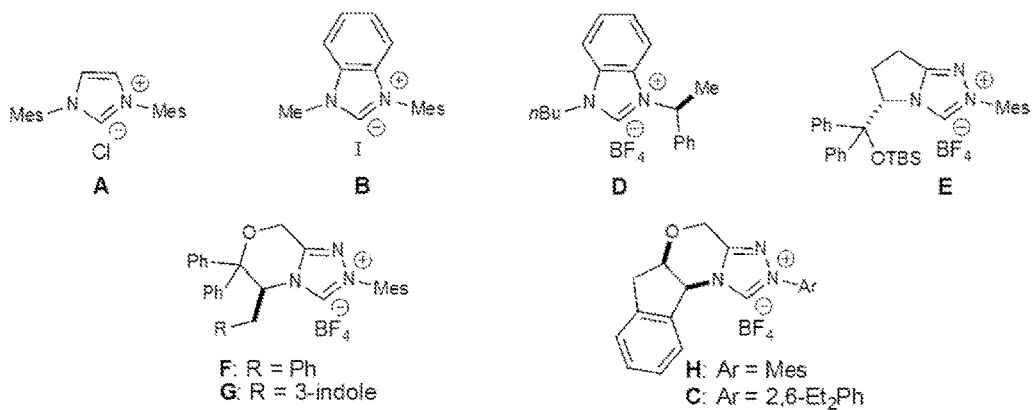

Figure 9

7-MEMBERED FUSED HETEROCYCLES AND METHODS OF THEIR SYNTHESIS

CROSS-REFERENCE TO RELATED PATENT APPLICATIONS

The present application claims the benefit of priority under 35 U.S.C. §119(e) to U.S. Provisional Patent Application No. 61/870,966, filed on Aug. 28, 2013, the content of which is incorporated herein by reference in its entirety.

STATEMENT REGARDING FEDERALLY SPONSORED RESEARCH OR DEVELOPMENT

This invention was made with government support under grant number R01 GM073072 awarded by the National Institutes of Health. The government has certain rights in the invention.

BACKGROUND

The field of the invention relates to 7-membered fused heterocycles and their methods of synthesis. In particular, the field of the invention relates to 7-membered fused heterocycles such as benzoxopinones, benzoxepanes, and benzoazepinones and methods of their synthesis.

Compounds comprising 7-membered fused heterocycles have been shown to be effective in a wide range of therapeutic applications. Benzoxepanes also are known to be central nervous system depressants. (See Porter et al., J. Psychopharmacology 2009, 203, 189). Benzodiazepine drugs such as Xanax® and Valium® are used to treat anxiety. (See Costanino et al., Benzodiazepines II; A Handbook; Spring: Berlin, 1989; Das et al., J. Med. Chem. 1992, 25 2610; and Floyd et al., J. Org. Chem. 1990, 5572). Further, benzazepinones are related to the FDA-approved drug diltiazem, which is a potent calcium channel blocker (Cardizem®) and SQ 31,486, a candidate to reduce myocardial ischemia for cardioprotective treatments. (See O'Connor et al., Fundam. Clin. Pharmacol. 1999, 13, 145; and Grover et al., J. Cardiovasc. Pharmacol. 1990, 16, 219).

Unfortunately, routes for synthesizing 7-membered fused heterocycles are scarce and the dearth of convergent strategies to access enantiopure scaffolds in good yields and selectivity has presumably hampered investigation of this class of compounds for its full therapeutic potential. Synthesis of 7-membered lactones through a formal [4+3] annulation has been reported recently. (See Lv et al., "N-Heterocyclic Carbene Catalyzed [4+3] Annulation of Enals and o-Quinone Methides: Highly Enantioselective Synthesis of Benzo-ε-Lactones." Angew. Chem. doi: 10.1002/ange.201303903, Jul. 1, 2013). However, this reported synthesis method is designed only for the use of two specific stable-ortho-quinone methides which limits the synthesis method to a short range of modifications.

Here, a new dual activation strategy for synthesizing 7-membered fused heterocycles is reported. The strategy integrates a first Lewis Base (i.e., an N-heterocyclic carbene (NHC)) with a second Lewis base. The synthesis procedure combines a NHC-bound homoenolate equivalent derived from an α,β-unsaturated aldehyde with a transient reactive ortho-quinone methide generated by desilylation of a stably protected ortho-phenoxy silyl ether in an enantioselective formal [4+3] fashion to obtain a 2-benzoxopinone. This strategy represents a new synthetic approach to obtain 7-membered fused heterocycles using a variety of common starting materials such as α,β-unsaturated aldehydes and substituted, stably protected ortho-phenoxy ethers. The overall approach provides a general blueprint for the integration of carbene catalysis with additional Lewis base activation modes to obtain a variety of new 7-membered fused heterocycles.

SUMMARY

Disclosed are 7-membered fused heterocycles and method of their synthesis. The 7-membered fused heterocycles include benzoxopinone compounds, as well as benzoxepane compounds and benzoazepinone compounds which optionally may be derived from the disclosed benzoxopinone compounds. Also disclosed are methods for synthesizing the disclosed 7-membered fused heterocycles including methods for synthesizing the disclosed benzoxopinone compounds, benzoxepane compounds, and benzoazepinone compounds.

The disclosed compounds may include benzoxopinone compounds having a formula:

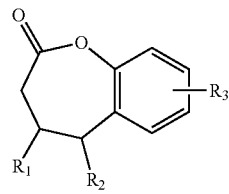

or a salt thereof, where $R_1$ is an aromatic system optionally selected from a group consisting of phenyl, naphthyl, and pyridinyl, which is optionally substituted with $C_1$-$C_6$ alkyl, halo, or $C_1$-$C_6$ alkoxy; $R_2$ is H or $C_1$-$C_6$ alkyl optionally substituted with halo, hydroxyl, phenyl, or halophenyl; and $R_3$ is H, an electron-donating group, or an alkyl group that forms a 5- or 6-membered ring with $R_2$.

The disclosed compounds also may include benzoxepane compounds which optionally may be prepared from the presently disclosed benzoxopinone compounds. The disclosed benzoxepane compounds may have a formula:

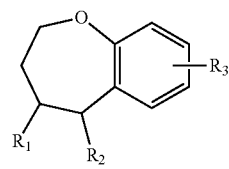

or a salt thereof, where $R_1$ is an aromatic system optionally selected from a group consisting of phenyl, naphthyl, and pyridinyl, which is optionally substituted with $C_1$-$C_6$ alkyl, halo, or $C_1$-$C_6$ alkoxy; $R_2$ is H or $C_1$-$C_6$ alkyl optionally substituted with halo, hydroxyl, phenyl, or halophenyl; and $R_3$ is H, an electron-donating group, or an alkyl group that forms a 5- or 6-membered ring with $R_2$.

The disclosed compounds also may include benzazepinone compounds which optionally may be prepared from the presently disclosed benzoxopinone compounds. The disclosed benzazepinone compounds may have a formula:

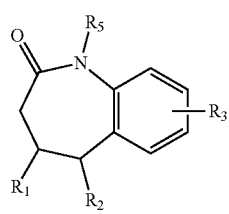

or a salt thereof, where $R_1$ is an aromatic system optionally selected from a group consisting of phenyl, naphthyl, and pyridinyl, which is optionally substituted with $C_1$-$C_6$ alkyl, halo, or $C_1$-$C_6$ alkoxy; $R_2$ is H or $C_1$-$C_6$ alkyl optionally substituted with halo, hydroxyl, phenyl, or halophenyl; $R_3$ is H, an electron-donating group, or an alkyl group that forms a 5- or 6-membered ring with $R_2$ with the proviso that, if $R_1$ is not substituted with $C_1$-$C_6$ alkyl, halo, or $C_1$-$C_6$ alkoxy, then at least one of $R_2$ and $R_3$ is not H; and $R_5$ is H, or $C_1$-$C_6$ alkyl optionally substituted with an amino group.

Also disclosed are methods for synthesizing 7-membered fused heterocycles including methods for synthesizing the disclosed benzoxopinone compounds, benzoxepane compounds, and benzoazepinone compounds. The disclosed methods for synthesizing 7-membered fused heterocycles typically include reacting a first Lewis base (e.g., an N-heterocyclic carbene (NHC)) with a second Lewis base.

The disclosed benzoxopinone compounds may be synthesized by a method that includes reacting one or more reaction mixtures that includes the following reaction components: (i) an unsaturated aldehyde compound (e.g., an α,β-unsaturated aldehyde); (ii) an N-heterocyclic carbene (NHC) as a first Lewis base; (iii) a substituted, protected, ortho-phenoxy ether compound; (iv) a second Lewis base (e.g., a source of F); (v) a base; and (vi) a solvent. The benzoxopinone compounds obtained from the disclosed methods optionally may be converted to corresponding benzoxepane derivatives or benzoazepinone derivatives using methods known in the art and described herein.

BRIEF DESCRIPTION OF THE FIGURES

FIG. 2. Table 1. NHC/Fluoride-promoted reaction of 1a and 2a[a]. [a] 1a (1 equiv), 2a (2 equiv), CsF (2 equiv), 18-crown ether-6 (2 equiv), base (30 mol %), THF (0.15 M in 1a), 23° C., 3 h. [b] reactions performed at −18° C. for 12 h. Er was determined by chiral stationary-phase high performance liquid chromatography (HPLC). Mes, 2,4,6-Me-$C_6H_2$.

FIG. 9. Optimization Table for the Formal [4+3] Cycloaddition with Ortho Quinonemethides.

DETAILED DESCRIPTION

Figure 1:
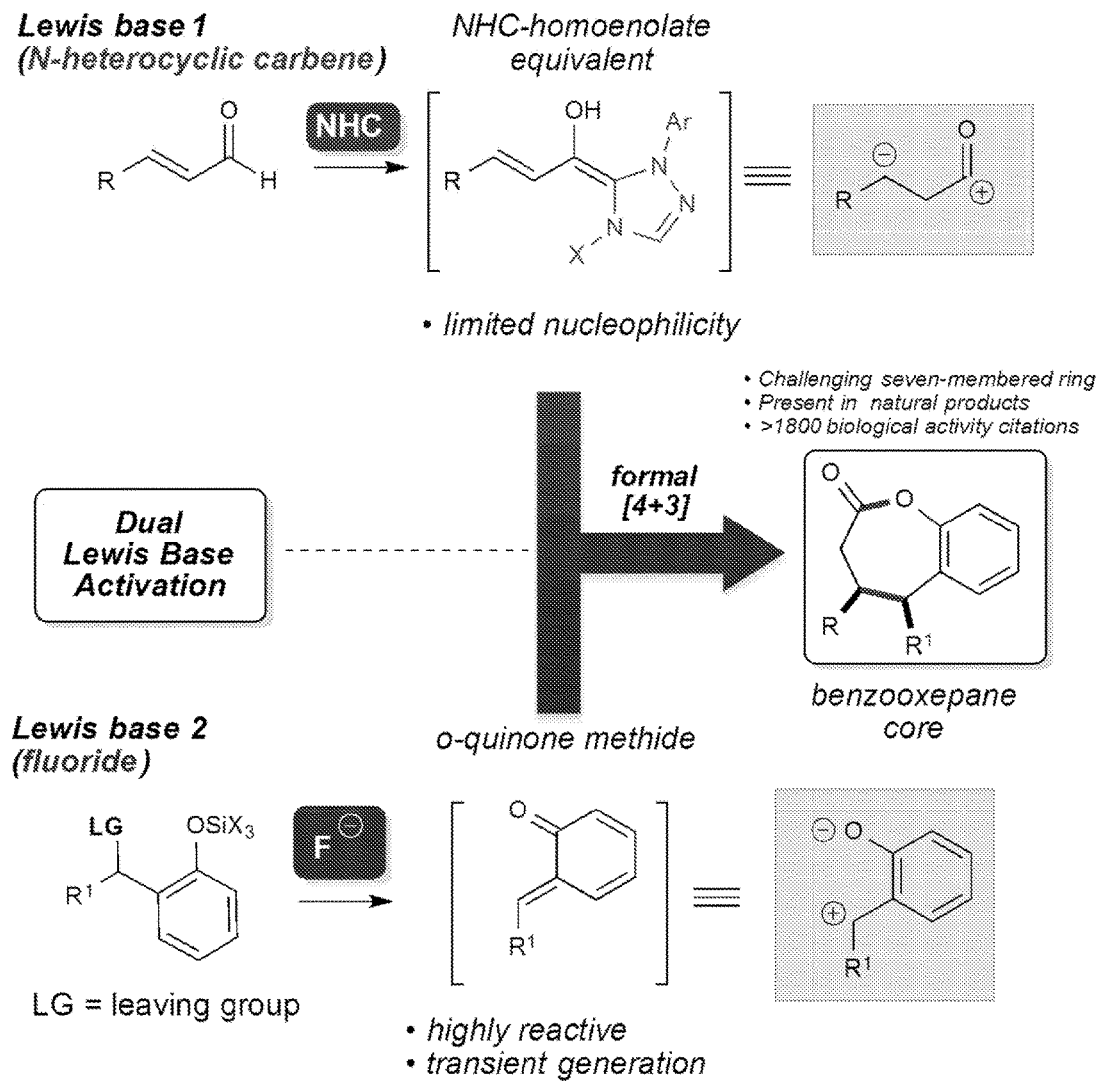
FIG. 1. Scheme 1. Dual Lewis base activation strategy.

The present invention is described herein using several definitions, as set forth below and throughout the application.

Unless otherwise specified or indicated by context, the terms "a", "an", and "the" mean "one or more." For example, "a substitution" should be interpreted to mean "one or more substitutions." Similarly, "a substituent group" should be interpreted to mean "one or more substituent groups."

As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion additional components other than the components recited in the claims. The term "consisting essentially of" should be interpreted to be partially closed and allowing the inclusion only of additional components that do not fundamentally alter the nature of the claimed subject matter.

Disclosed are 7-membered fused heterocycles including benzoxopinone compounds, as well as benzoxepane compounds and benzoazepinone compounds that optionally may be derived from the disclosed benzoxopinone compounds. The disclosed compounds may be further described as follows.

The disclosed benzoxopinone compounds typically have a formula:

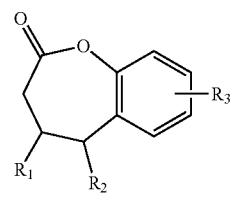

or a salt thereof, where $R_1$ is an aromatic system optionally selected from a group consisting of phenyl, naphthyl, and pyridinyl, which is optionally substituted with $C_1$-$C_6$ alkyl, halo, or $C_1$-$C_6$ alkoxy; $R_2$ is H or $C_1$-$C_6$ alkyl optionally substituted with halo, hydroxyl, phenyl, or halophenyl; and $R_3$ is H, an electron-donating group, or an alkyl group that forms a 5- or 6-membered ring with $R_2$.

The disclosed benzoxopinone compounds further may exhibit stereochemistry at one or more positions. For example, the disclosed benzoxopinone compounds may exhibit stereochemistry with respect to the $R_1$ and/or $R_2$ substituent and may have a formula:

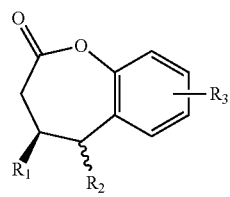

or specifically

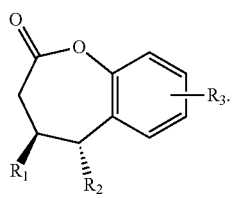

The disclosed benzoxopinone compounds typically include an $R_1$ substituent that is an aromatic system. Suitable aromatic systems may include, but are not limited to, phenyl, naphthyl, and pyridinyl, which optionally may be substituted at one or more positions with $C_1$-$C_6$ alkyl, halo, or $C_1$-$C_6$ alkoxy.

The disclosed benzoxopinone compounds may include an $R_3$ substituent that is H, a 5- or 6-membered ring with $R_2$, or an electron-donating group. Suitable electron-donating groups may include, but are not limited to, $C_1$-$C_6$ alkyl and $C_1$-$C_6$ alkoxy.

Exemplary benzoxopinone compounds as contemplated herein may include, but are not limited to compounds having a formula selected from a group consisting of:

(3a)
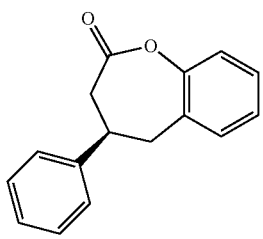
, (3b)
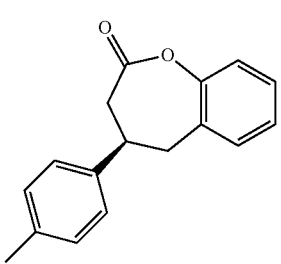
, (3c)
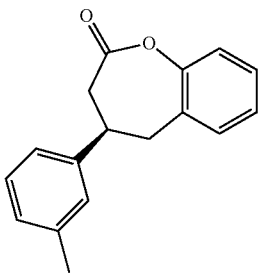
, (3d)
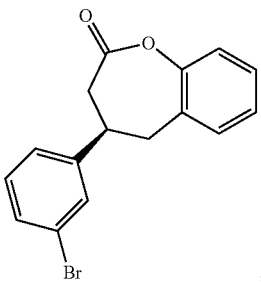
, (3e)
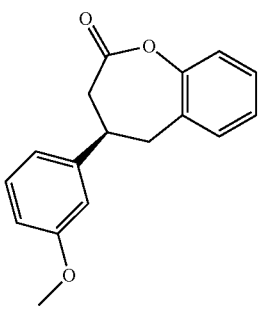
, (3f)
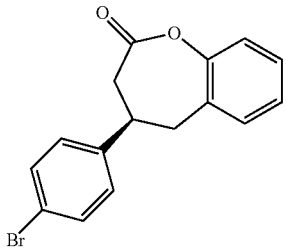
, (3g)
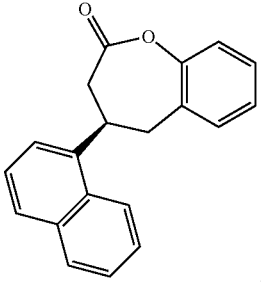
,

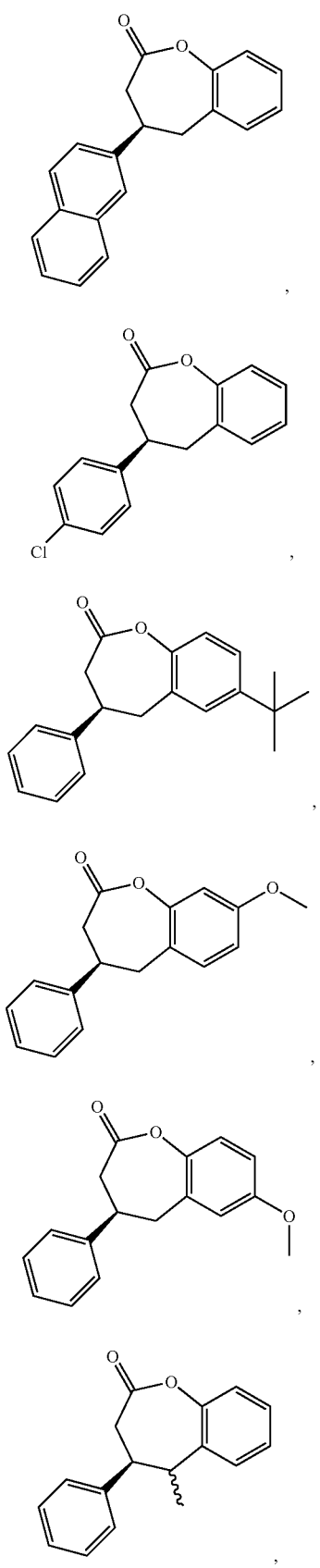

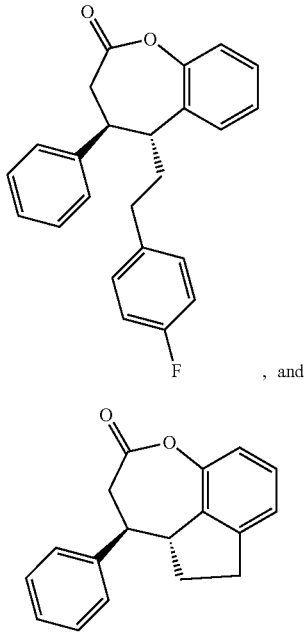

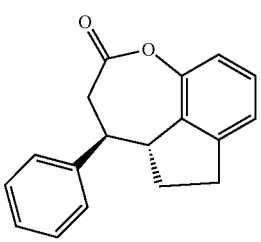

Also disclosed are benzoxepane compounds which optionally may be derived from the disclosed benzoxopinone compounds via a reaction that removes the carbonyl oxygen in the seven-membered ring. The disclosed benzoxepane compounds may have a formula:

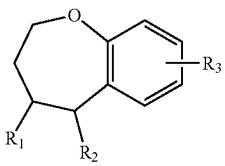

or a salt thereof, where R is an aromatic system optionally selected from a group consisting of phenyl, naphthyl, and pyridinyl, which is optionally substituted with $C_1$-$C_6$ alkyl, halo, or $C_1$-$C_6$ alkoxy; $R_2$ is H or $C_1$-$C_6$ alkyl optionally substituted with halo, hydroxyl, phenyl, or halophenyl; and $R_3$ is H, an electron-donating group, or an alkyl group that forms a 5- or 6-membered ring with $R_2$.

The benzoxepane compounds also may exhibit stereochemistry at one or more positions. For example, the disclosed benzoxepane compounds may exhibit stereochemistry with respect to the $R_1$ and/or $R_2$ substituent and may have a formula:

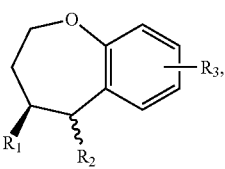

or specifically

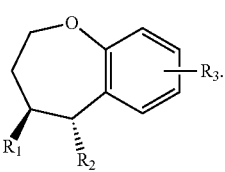

The disclosed benzoxepane compounds typically include an $R_1$ substituent that is an aromatic system. Suitable aromatic systems may include, but are not limited to, phenyl, naphthyl, pyridinyl, which optionally may be substituted at one or more positions with $C_1$-$C_6$ alkyl, halo, or $C_1$-$C_6$ alkoxy.

The disclosed benzoxepane compounds may include an $R_3$ substituent that is H, a 5- or 6-membered ring with $R_2$, or an electron-donating group. Suitable electron-donating groups may include, but are not limited to, $C_1$-$C_6$ alkyl and $C_1$-$C_6$ alkoxy.

Exemplary benzoxepane compounds as contemplated herein may include, but are not limited to compounds having a formula selected from a group consisting of:

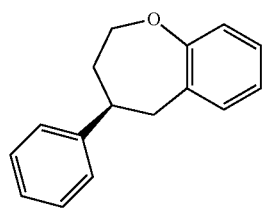
(3a'),

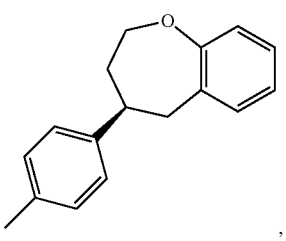
(3b'),

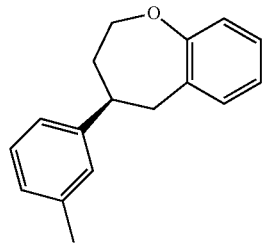
(3c'),

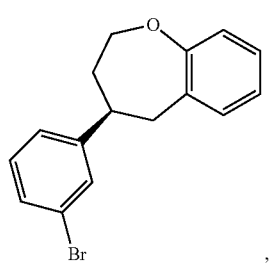
(3d'),

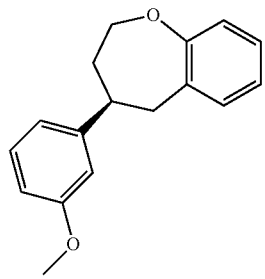
(3e'),

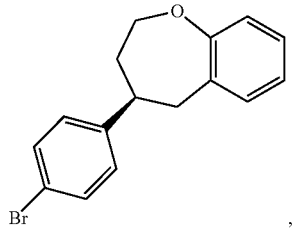
(3f'),

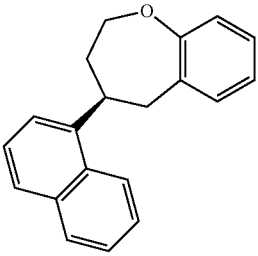
(3g'),

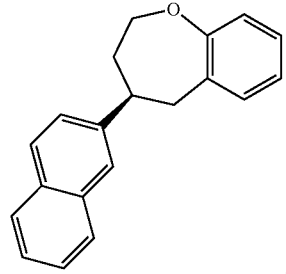
(3h'),

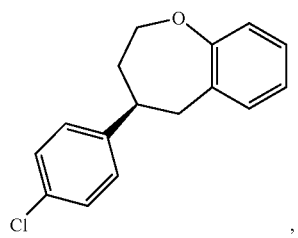
(3i'),

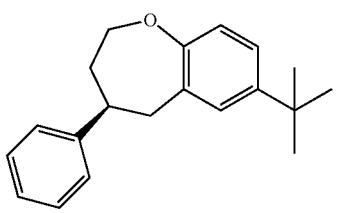
(3j'),

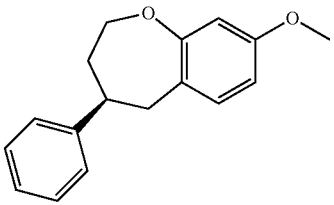
(3k'),

-continued

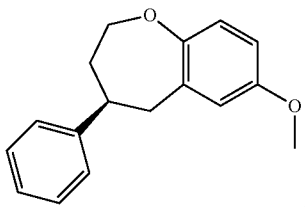
(3l′)

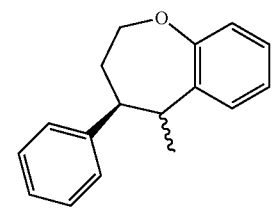
(3m′)

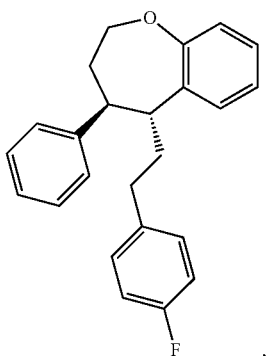
(3n′)
, and

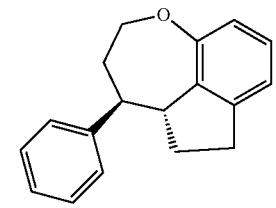
(3o′)

Also disclosed are benzoazepinone compounds which optionally may be derived from the disclosed benzoxopinone compounds via a reaction that replaces the oxo group of the seven-membered group with a nitrogen atom. The disclosed benzoazepinone compounds may have a formula:

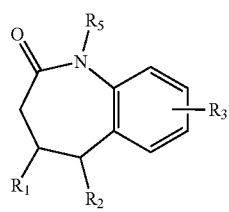

or a salt thereof, where, $R_1$ is an aromatic system selected from a group consisting of phenyl, naphthyl, and pyridinyl, and optionally substituted with $C_1$-$C_6$ alkyl, halo, or $C_1$-$C_6$ alkoxy; $R_2$ is H or $C_1$-$C_6$ alkyl optionally substituted with halo, hydroxyl, phenyl, or halophenyl; $R_3$ is H, an electron-donating group, or an alkyl group that forms a 5- or 6-membered ring with $R_2$ with the proviso that, if $R_1$ is not substituted with $C_1$-$C_6$ alkyl, halo, or $C_1$-$C_6$ alkoxy, then at least one of $R_2$ and $R_3$ is not H; and $R_5$ is H, or $C_1$-$C_6$ alkyl optionally substituted with an amino group.

The benzazepinone compounds also may exhibit stereochemistry at one or more positions. For example, the disclosed benzazepinone compounds may exhibit stereochemistry with respect to the $R_1$ and/or $R_2$ substituent and may have a formula:

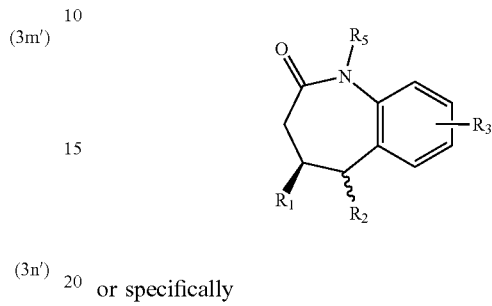

or specifically

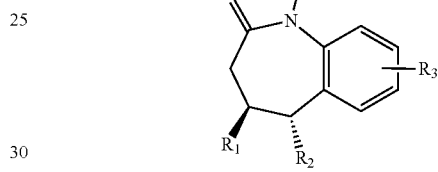

The disclosed benzazepinone compounds typically include an $R_3$ substituent that is H, an alkyl group that forms a 5- or 6-membered ring with $R_2$, or an electron-donating group. Suitable electron-donating groups may include, but are not limited to, $C_1$-$C_6$ alkyl and $C_1$-$C_6$ alkoxy.

Exemplary benzazepinone compounds as contemplated herein may include, but are not limited to compounds having a formula selected from a group consisting of:

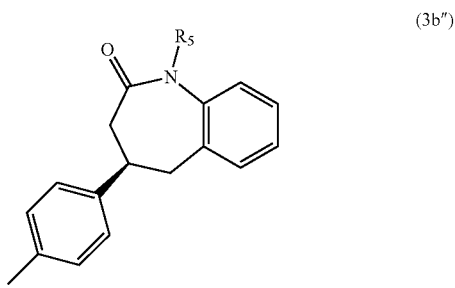
(3b″)

,

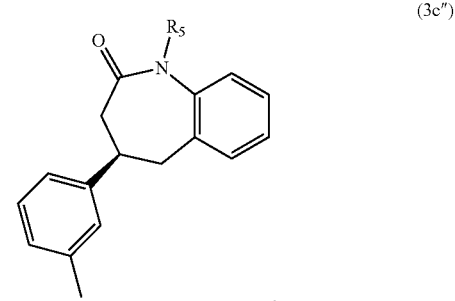
(3c″)

,

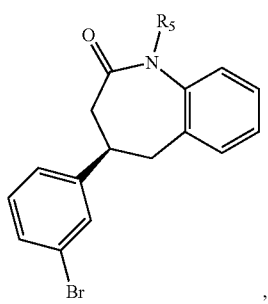
(3d″)
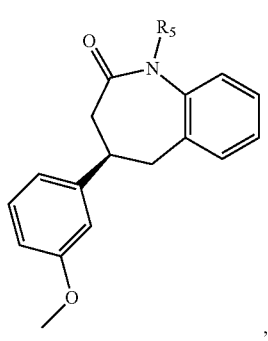
(3e″)
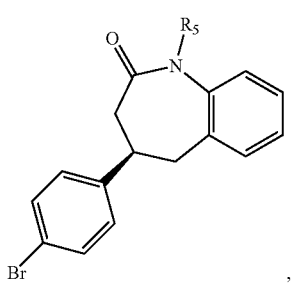
(3f″)
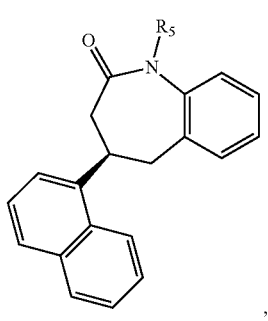
(3g″)
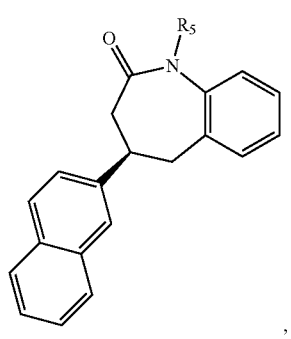
(3h″)
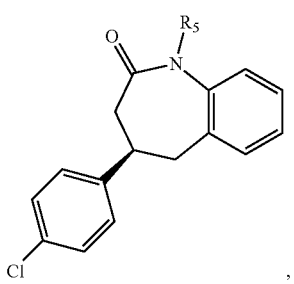
(3i″)
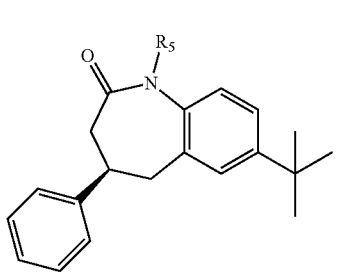
(3j″)
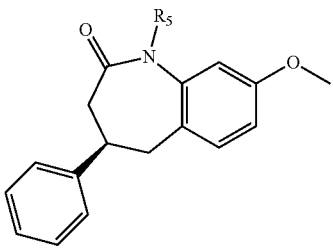
(3k″)
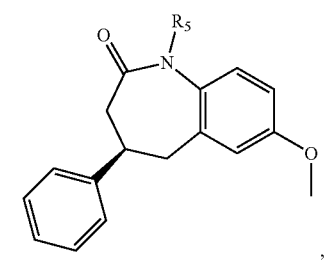
(3l″)
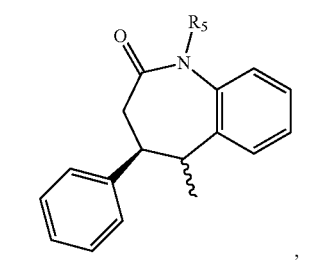
(3m″)

-continued

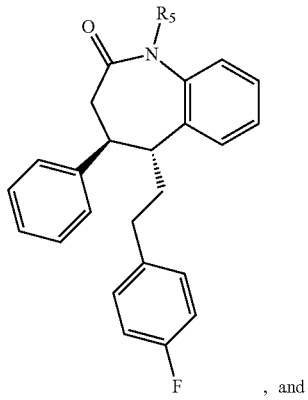
(3n″)
, and

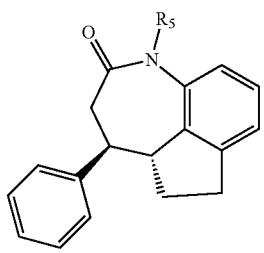
(3o″)

Also disclosed are methods for synthesizing 7-membered fused heterocycles including methods for synthesizing the disclosed benzoxopinone compounds, benzoxepane compounds, and benzoazepinone compounds. The disclosed methods for synthesizing 7-membered fused heterocycles typically include reacting a first Lewis base (e.g., an N-heterocyclic carbene (NHC)) with a second Lewis base which may be further described as follows.

The disclosed benzoxopinone compounds may be synthesized by a method that includes reacting one or more reaction mixtures that includes the following reaction components: (i) an unsaturated aldehyde compound (e.g., an α,β-unsaturated aldehyde); (ii) an N-heterocyclic carbene (NHC) as a first Lewis base; (iii) a substituted, protected, ortho-phenoxy ether compound; (iv) a second Lewis base (e.g., a source of F); (v) a base; and (vi) a solvent. In particular, methods for synthesizing the disclosed benzoxopinone compounds may include reacting one or more reaction mixtures that include the following components:

(i) an unsaturated aldehyde compound, e.g.,

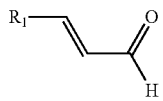

wherein $R_1$ is an aromatic system;

(ii) an N-heterocyclic carbene (NHC);

(iii) a substituted, protected, ortho-phenoxy ether compound, e.g.,

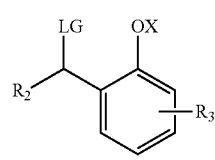

wherein:
  $R_2$ is H or $C_1$-$C_6$ alkyl optionally substituted with halo, hydroxyl, phenyl, or halophenyl;
  $R_3$ is H, an electron-donating group, or an alkyl group that forms a 5- or 6-membered ring with $R_2$;
  LG is a leaving group; and
  X is a protecting group;

(iv) a source of F;
(v) a base; and
(vi) a solvent.

In the method, a NHC-bound homoenolate equivalent derived from the α,β-unsaturated aldehyde may be generated and reacted with a transient reactive ortho-quinone methide, generated by unprotecting the protected, ortho-phenoxy ether compound, in an enantioselective formal [4+3] fashion to obtain a 2-benzoxopinone. The benzoxopinone compounds obtained from the disclosed methods optionally may be converted to corresponding benzoxepane derivatives or benzoazepinone derivatives using methods known in the art and described herein.

The disclosed methods may utilize an unsaturated aldehyde compound (i.e., an α,β-unsaturated aldehyde) as a precursor for forming the disclosed benzoxopinone compounds. The unsaturated aldehyde compound utilized in the methods typically includes an aromatic system as an $R_1$ substituent. Suitable aromatic systems may include, but are not limited to phenyl, naphthyl, and pyridinyl, which optionally are substituted at one or more positions with $C_1$-$C_6$ alkyl, halo, or $C_1$-$C_6$ alkoxy.

The synthesis methods also utilize an N-heterocyclic carbene (NHC) compound also referred to as a first Lewis base. In the synthesis method, the NHC compound forms an NHC-homoenolate with the unsaturated aldehyde compound. Suitable NHC compounds for use in the disclosed methods may include, but are not limited to, compounds, or salts thereof, having a formula:

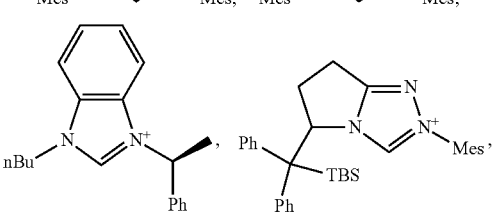

-continued

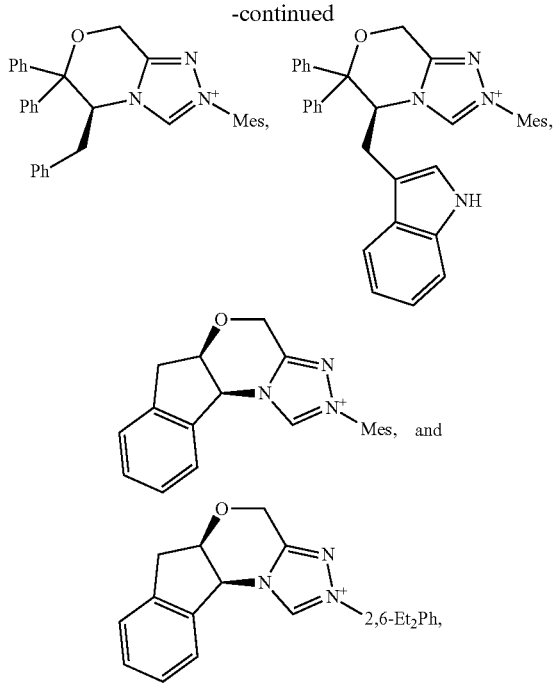

where "Mes" is mesityl, "nBu" is n-butyl, "Ph" is phenyl, and "Et" is ethyl.

The disclosed methods may utilize a substituted, stably protected ortho-phenoxy ether as a precursor for forming the disclosed benzoxopinone compounds. The ortho-phenoxy ether is substituted with a leaving group (LG). Suitable leaving groups may include, but are not limited to, halides, such as Br⁻ or Cl⁻ and (preferably Br⁻) and sulfonate esters (e.g., tosylates and mesylates).

The ortho-phenoxy ether is stably protected via a protecting group (e.g., an alcohol-protecting group). Suitable protecting groups may include, but are not limited to silyl ethers, and preferably tert-butyldimethylsilyl (TBDMS), tri-iso-propylsilyl (TIPS), and tri-iso-propylsilyloxymethyl (TOM).

In addition to the first Lewis base (i.e., the NHC compound), the disclosed methods also use a second Lewis base which may be F. As a source for F, the reaction mixture may include a fluoride salt such as an alkali metal salt. Where the reaction mixture includes an alkali metal salt, the reaction mixture also may include a complexing agent for the alkali metal cation. Suitable complexing agents may include, but are not limited to, crown ethers such as 18-crown-6.

The reaction mixture typically includes a base. Suitable bases may include but are not limited to carbonate salts (e.g., $Cs_2CO_2$), acetate salts ($C_2OAc$, n-$Bu_4N.OAc$), amines (e.g., $Et_3N$), pyridine, alkoxides (e.g., CsOtBu), and benzoate salts (e.g., 4-$NO_2$—$C_6H_4COONa$).

The reaction mixture includes a solvent suitable for dissolving the reaction components including the α,β-unsaturated aldehyde and the substituted, stably protected ortho-phenoxy ether. Suitable solvents may include, but are not limited to tetrahydrofuran (THF).

ILLUSTRATIVE EMBODIMENTS

The following embodiments are illustrative and do not limit the scope of the claimed subject matter.

Embodiment 1

A compound having a formula:

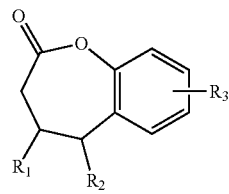

or a salt thereof, wherein: $R_1$ is an aromatic system optionally selected from a group consisting of phenyl, naphthyl, and pyridinyl, and optionally substituted with $C_1$-$C_6$ alkyl, halo, or $C_1$-$C_6$ alkoxy; $R_2$ is H or $C_1$-$C_6$ alkyl optionally substituted with halo, hydroxyl, phenyl, or halophenyl; and $R_3$ is H, an electron-donating group, or an alkyl group that forms a 5- or 6-membered ring with $R_2$.

Embodiment 2

The compound of embodiment 1 having a formula:

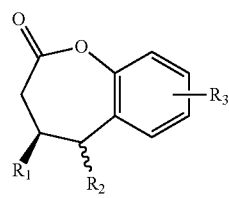

Embodiment 3

The compound of embodiment 1 or 2 having a formula:

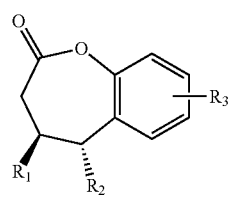

Embodiment 4

The compound of any of the preceding embodiments, wherein $R_1$ is an aromatic system selected from a group consisting of phenyl, naphthyl, and pyridinyl, optionally substituted with $C_1$-$C_6$ alkyl, halo, or $C_1$-$C_6$ alkoxy.

Embodiment 5

The compound of any of the preceding embodiments having a formula selected from a group consisting of:

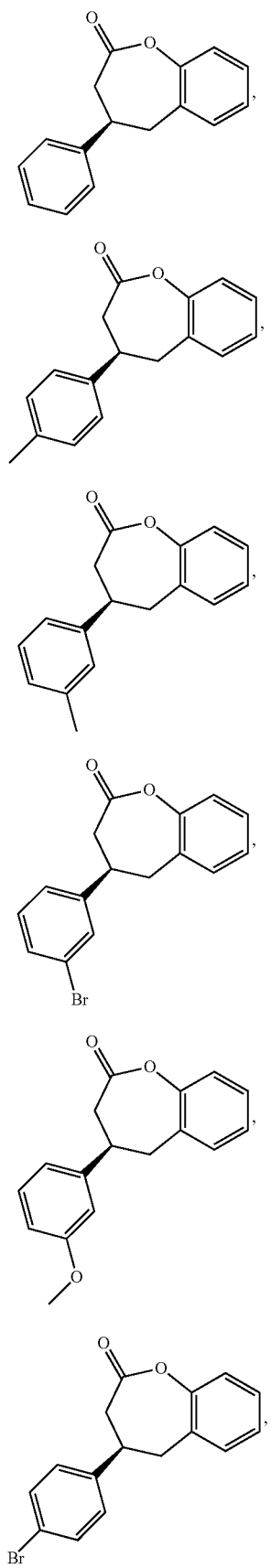
(3a)
(3b)
(3c)
(3d)
(3e)
(3f)
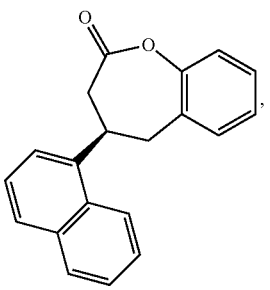
(3g)
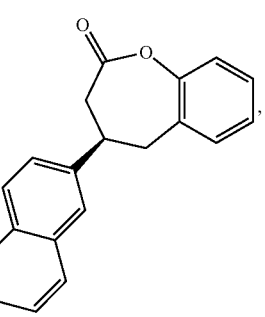
(3h)
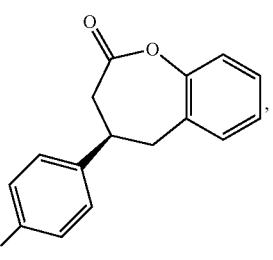
(3i)
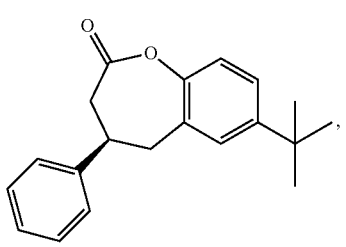
(3j)
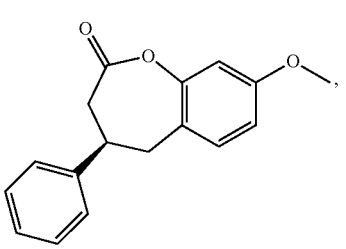
(3k)
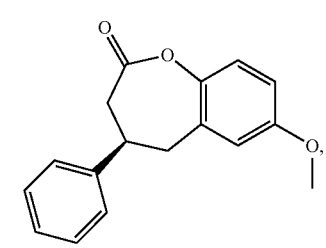
(3l)

-continued (3m)

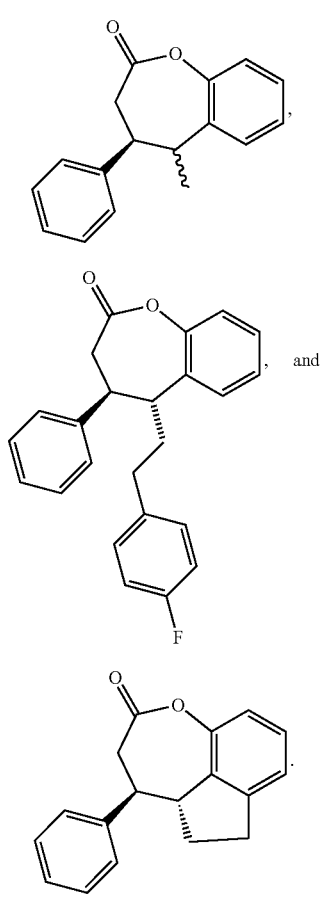

(3n)

(3o)

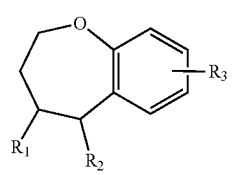

Embodiment 6

The compound of any of the preceding embodiments, wherein $R_3$ is H or an electron-donating group selected from a group consisting of $C_1$-$C_6$ alkyl and $C_1$-$C_6$ alkoxy.

Embodiment 7

A compound having a formula:

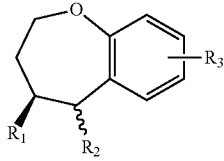

or a salt thereof, wherein: $R_1$ is an aromatic system optionally selected from a group consisting of phenyl, naphthyl, and pyridinyl, and optionally substituted with $C_1$-$C_6$ alkyl, halo, or $C_1$-$C_6$ alkoxy; $R_2$ is H or $C_1$-$C_6$ alkyl optionally substituted with halo, hydroxyl, phenyl, or halophenyl; and $R_3$ is H, an electron-donating group, or an alkyl group that forms a 5- or 6-membered ring with $R_2$.

Embodiment 8

The compound of embodiment 7 having a formula:

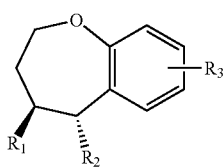

Embodiment 9

The compound of embodiment 7 or 8 having a formula:

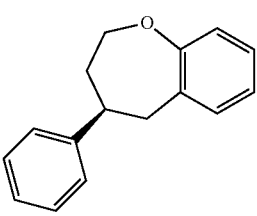

Embodiment 10

The compound of any embodiments 7-9, wherein $R_1$ is an aromatic system selected from a group consisting of phenyl, naphthyl, and pyridinyl, optionally substituted with $C_1$-$C_6$ alkyl, halo, or $C_1$-$C_6$ alkoxy.

Embodiment 11

The compound of any of embodiments 7-10 having a formula selected from a group consisting of:

(3a′)

(3b′)

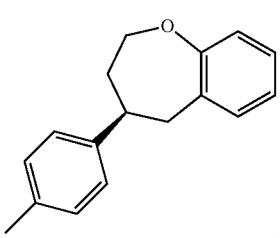

-continued
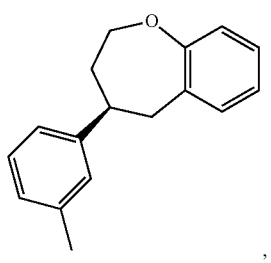
(3c′)
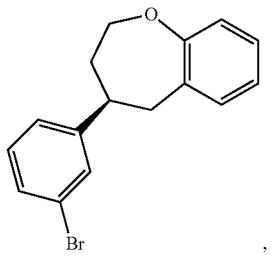
(3d′)
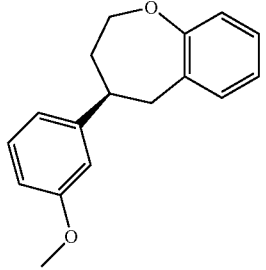
(3e′)
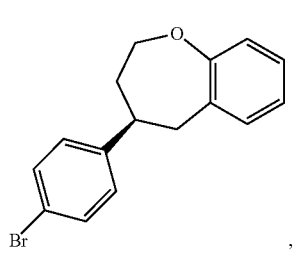
(3f′)
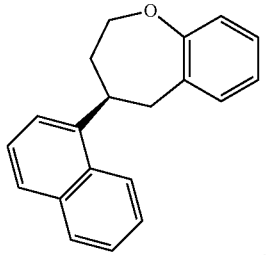
(3g′)
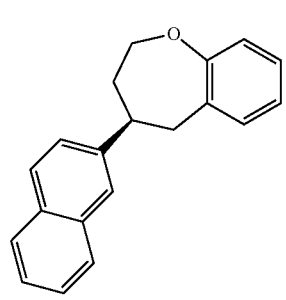
(3h′)
-continued
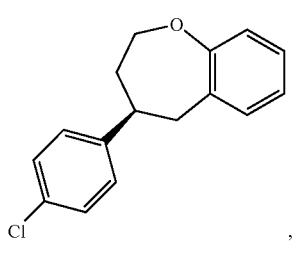
(3i′)
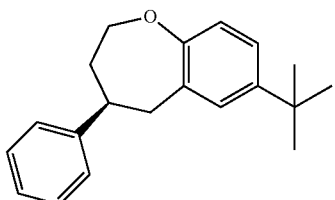
(3j′)
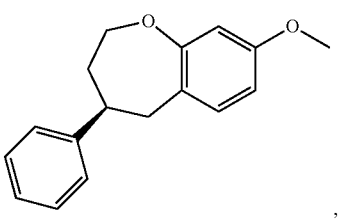
(3k′)
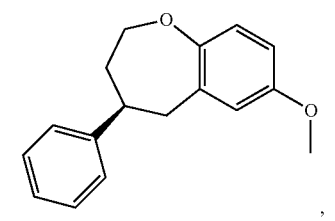
(3l′)
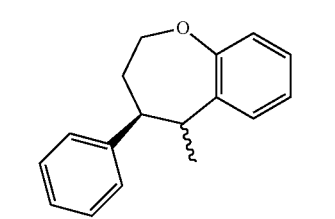
(3m′)
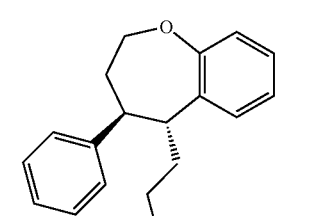
(3n′)
, and (3o′)
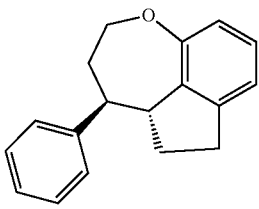

Embodiment 12

The compound of any of embodiments 7-11, wherein $R_3$ is H or an electron-donating group selected from a group consisting of $C_1$-$C_6$ alkyl and $C_1$-$C_6$ alkoxy.

Embodiment 13

A compound having a formula:

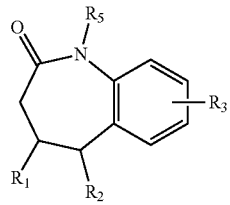

or a salt thereof, wherein: $R_1$ is an aromatic system optionally selected from a group consisting of phenyl, naphthyl, and pyridinyl, and optionally substituted with $C_1$-$C_6$ alkyl, halo, or $C_1$-$C_6$ alkoxy; $R_2$ is H or $C_1$-$C_6$ alkyl optionally substituted with halo, hydroxyl, phenyl, or halophenyl; $R_3$ is H, an electron-donating group, or an alkyl group that forms a 5- or 6-membered ring with $R_2$ with the proviso that if $R_1$ is not substituted with $C_1$-$C_6$ alkyl, halo, or $C_1$-$C_6$ alkoxy then at least one of $R_2$ and $R_3$ is not H; and $R_5$ is H, or $C_1$-$C_6$ alkyl optionally substituted with an amino group.

Embodiment 14

The compound of embodiment 13 having a formula:

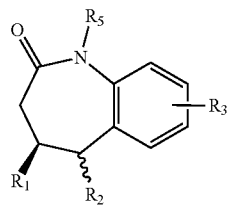

Embodiment 15

The compound of embodiment 13 or 14 having a formula:

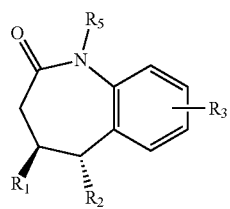

Embodiment 16

The compound of any of embodiments 13-15 having a formula selected from a group consisting of:

(3b″)

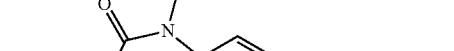
(3c″)

(3d″)

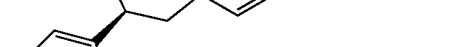
(3e″)

(3f″)

Embodiment 17

The compound of any of embodiments 13-16, wherein $R_3$ is H or an electron-donating group selected from a group consisting of $C_1$-$C_6$ alkyl and $C_1$-$C_6$ alkoxy.

Embodiment 18

A method for preparing the compound of any of the foregoing embodiments, the method comprising reacting one or more reaction mixtures comprising: (i)

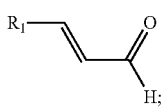

wherein R₁ is as defined as in the above embodiments; (ii) an a first Lewis base (e.g., N-heterocyclic carbene (NHC)); (iii)

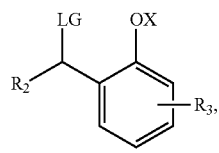

wherein: R₂ and R₃ are as defined as in the above embodiments; LG is a leaving group; and X is a protecting group; (iv) a second Lewis base (e.g., a source of F⁻); (v) a base; and (vi) a solvent.

Embodiment 19

The method of embodiment 18, wherein the NHC is selected from a group of compounds or salts thereof having a formula:

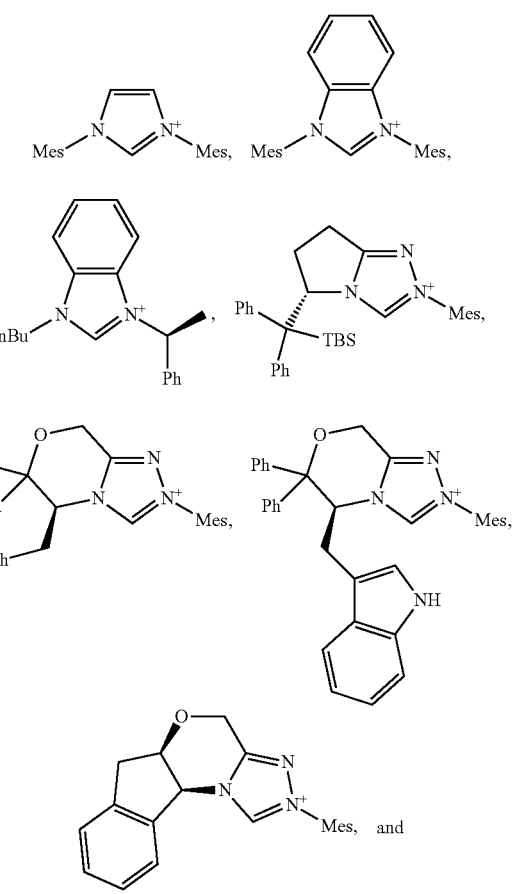

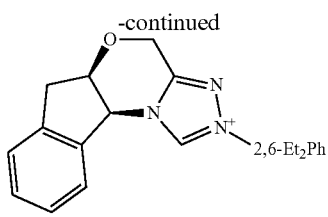

Embodiment 20

The method of embodiment 18 or 19, wherein LG is Br⁻ or Cl⁻ or a sulfonate esters (e.g., tosylates and mesylates).

Embodiment 21

The method of any of embodiments 18-20, wherein the protecting group is an alcohol-protecting group, preferably a silyl ether, more preferably tert-butyldimethylsilyl (TB-DMS), tri-iso-propylsilyl (TIPS), and tri-iso-propylsilyloxymethyl (TOM).

Embodiment 22

The method of any of embodiments 18-21, wherein the second Lewis base is a source of F⁻ and the source of F⁻ is an alkali metal salt.

Embodiment 23

The method of any of embodiments 18-21, wherein the second Lewis base is a source of F⁻ and the source of F⁻ is an alkali metal salt and a complexing agent for an alkali metal cation.

Embodiment 24

The method of embodiments 23, wherein the complexing agent is a crown ether, preferably 18-crown-6.

Embodiment 25

A pharmaceutical composition comprising a compound of any of the foregoing embodiments and optionally a carrier, excipient, or diluent.

EXAMPLES

The following example is illustrative and should not be interpreted to limit the claimed subject matter. Reference is made to Izquierdo et al., "A Dual Lewis Base Activation Strategy for Enantioselective Carbene-Catalyzed Annulations," J. Am. Chem. Soc., Vol. 135, No. 29, pages 10634-10637, Jul. 5, 2013, and the corresponding Supporting Information, the contents of which are incorporated herein by reference in their entireties.

Abstract

A dual activation strategy integrating NHC catalysis and a second Lewis base has been developed. NHC-hound homoenolate equivalents derived from α,β-unsaturated aldehydes combine with transient reactive o-quinone methides in an enantioselective formal [4+3] fashion to access 2-benzoxopinones. The overall approach provides a general blueprint for the integration of carbene catalysis with additional Lewis base activations modes.

Introduction

The advances made by employing chiral catalysts to forge new carbon-carbon and carbon-heteroatom bonds with high levels of stereoselectivity have provided efficient access to new chiral molecules in high enantiomeric excess with broad potential uses.[1] A majority of these strategies rely on a single activation mode, such as Lewis base[2] or acid[3] catalysis, enamine/iminium ion catalysis,[4] hydrogen bond donor/Brønsted acid catalysis,[5] σ-bond activation,[6] and an immense variety of transition metal chemistry.[7] With proper substrate and catalyst design, these diverse sets of reactions access a myriad of distinct compound classes with dizzying arrays of functional groups and ring systems. However, there are inherent limitations of reactivity and selectivity within each activation "sphere". In many cases, some substrates are simply not reactive enough to engage with a catalyst or the combination of starting materials is ineffective due to poor pairing of electronic parameters (i.e., electrophilicity/nucleophilicity).

N-Heterocyclic carbenes (NHCs) are versatile Lewis bases capable of promoting a variety of powerful and unconventional bond-forming processes, including acyl anion reactions, homoenolate equivalents, enolate additions and oxidations.[8] Inspired by early carbonyl anion catalysis,[9] one particularly versatile reaction mode is the NHC-homoenolate described in 2004.[10] This process provides a metal free approach to access β-anionic carbonyl systems and we have been exploring this activation mode for the development of multiple new reactions. Carbene catalysis typically entails formal [n+m]-type cycloaddition transformations by virtue of the mechanistic pathway and catalyst turnover (see below). This distinct feature provides a powerful platform for convergent ring formation strategies, so long as the electrophilic partner is reactive enough to engage the NHC-homoenolate in an initial sigma bond-forming event. While it is clear that these homoenolates can undergo additions to reactive electrophilic C=X π systems, such as aldehydes and imines, many classes of less reactive potential partners typically result in no productive interactions. New opportunities in carbene catalysis over the next decade will undoubtedly focus on moving past these standard π systems, but the current challenge remains for identifying what innovative concepts will expedite this evolution.

We hypothesized if it were possible to drive NHC-generated homoenolate methodology in new directions by integrating a second mode of activation which could produce more reactive electrophiles beyond stable C=O or C=N π bonds. We successfully integrated Lewis acid activation modes with NHC catalysis[11] and utilized this knowledge base to consider additional activation modes such as in situ, Lewis base-promoted electrophile creation (Scheme 1, FIG. 1). There have been limited examples of combining carbene catalysis with Lewis acids,[11,12] as well as Bronsted acids,[13] but to date, the idea of a utilizing a second Lewis base activation mode in conjunction with NHCs remains an underexplored strategy.

To pursue this new strategy, we proposed that the production of highly reactive o-quinone methides (o-QMs) generated under fluoride conditions through a desilylation/elimination cascade could be combined with an NHC-homoenolate catalytic cycle.[14] o-QMs are considerably more reactive than regular α,β-unsaturated ketones and esters since nucleophilic attack on the external carbon produces an aromatic alcohol (phenol/phenoxide) and this aromatization process of the ring is a highly thermodynamically favorable. Although stable o-QMs are known, the more reactive variants are useful intermediates in synthesis and can be produced in situ through the addition of light, oxidants, or fluoride.[15] In the context of this new NHC reaction, we desired access to as many different possible o-QM structures through an in situ approach (e.g., fluoride), thereby ensuring the broadest potential substrate scope at the onset of these studies should our concept prove successful. However, the fleeting nature of many of these species combined with their propensity to undergo dimerization via a [4+2] pathway or react with even weak nucleophiles were possible obstacles.[15c] If successful, the productive realization of this new dual Lewis base activation strategy would produce seven-membered lactones (2-benzoxopinones) which are found in natural products and are the core constituents for numerous small molecules with broad biological activity.[16]

We initially considered four challenges of this potential reaction: 1) the compatibility of the second Lewis base with the in situ generated NHC, 2) the compatibility of the highly reactive o-QM with a nucleophilic NHC catalyst, 3) the potentially unproductive behavior of transient o-QMs under the reaction conditions (e.g., dimerization), and 4) the requirement of equilibrium populations of both NHC-bound homoenolate and o-QM to lead to a productive bond-forming process. With these issues in mind, major questions remained at the onset about the suitable fluoride source to promote the optimal rate of o-QM production in situ. Guided by these issues of compatibility and competing rates, extensive tuning of the major reaction parameters (catalyst structure, base composition, fluoride source) was required to address the complex and interconnected issues above. To our delight, the proper rate of o-QM production was successfully achieved through the use of a crown ether/fluoride combination with a t-butyldimethylsilyl (TBS) phenol substrate (Table 1, FIG. 2). For the initial set of investigations, the bromide leaving group in the presence of $Cs_2CO_3$ provided the encouraging levels of conversion to the desired product, albeit in low yield, with achiral imidazolium- and benzimidazolium-derived carbenes (prepared in situ from A and B, respectively, see Table 1, FIG. 2, entries 1-3).[17]

A competing reaction pathway was the generation of 4a, which forms from the protonation of the NHC-homoenolate followed by a formal [4+2] pathway (see below for reaction pathway discussions). With CsOAc as base and chiral triazolium NHC C, good levels of enantioselectivity were observed (91:9 er) with only moderate yield (47%) (see Table 1, FIG. 2, entry 4). A further examination of the o-QM precursor indicated that triisopropyl (TIPS) can also facilitate the reaction in the presence of fluoride without major differences in the results (see Table 1, FIG. 2, entry 4 vs. 6), but still only <50% yields. In contrast, the more labile trimethylsilylphenol (TES protecting group) did not afford product (see Table 1, FIG. 2, entry 7).

The leaving group to expedite elimination and produce o-QM in situ can be either bromide or chloride without noticeable differences in overall reactivity. The optimal combination of CsF/18-crown-6 for o-QM generation and n-$Bu_4$N.OAc as a mild base provided the formal [4+3] lactone product was obtained in moderate yield and excellent enantioselectivity (see Table 1, FIG. 2, entry 8, 62%, 92:8 er). The lowering of the reaction temperature to −18° C. from 0° C. increased the time necessary for consumption of 1a, but also provided better stereoselectivity (dr=5.5:1, er=96:4, entry 9).[18]

Figure 3:
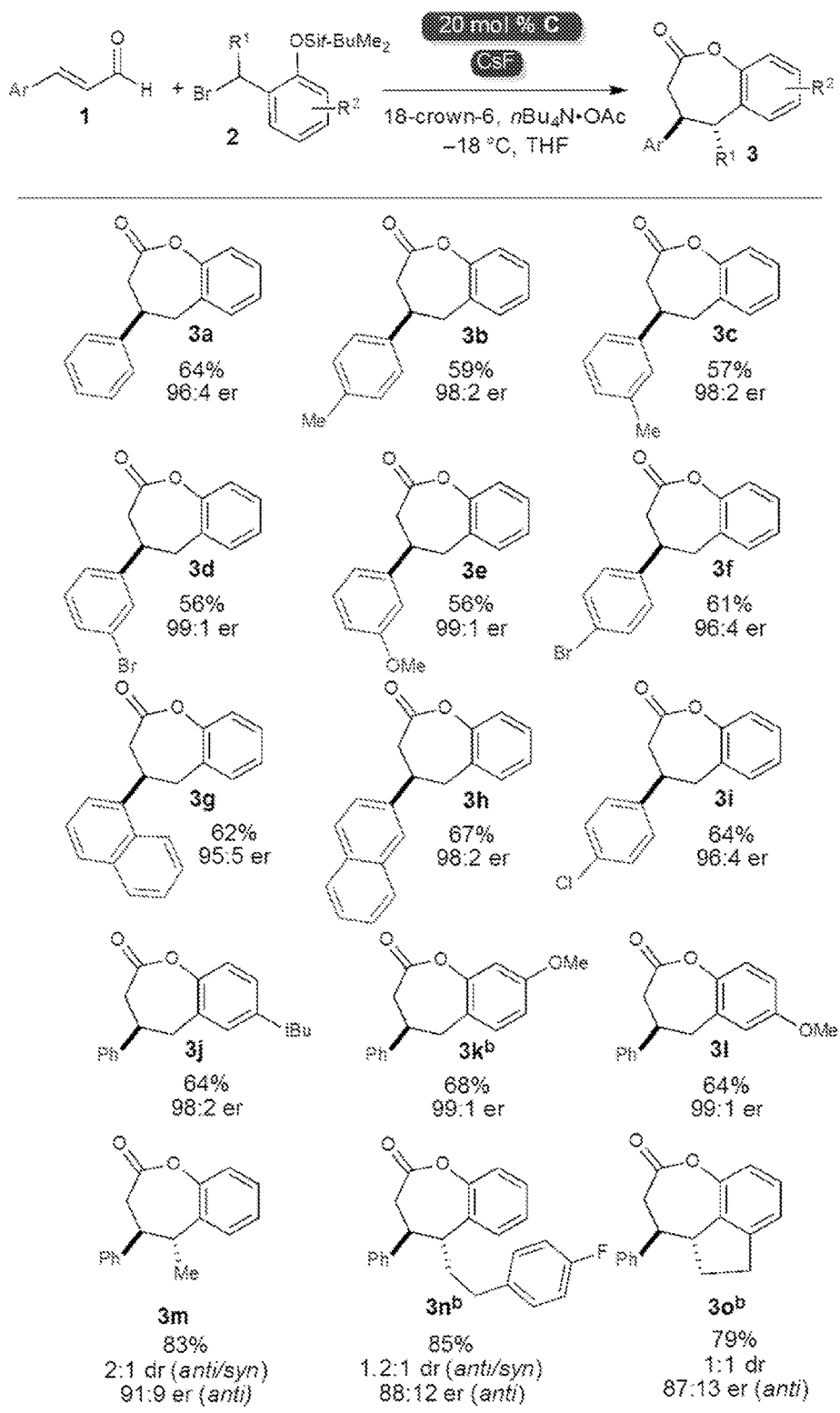
FIG. 3. Table 2. Scope of dual activation formal [4+3] annulation[a]. [a] Reactions were performed at 0.4 mmol with 1 equiv of 1, 2 equiv of 2, 0.3 equiv base, 2 equiv CsF and 2 equiv crown ether in THF (0.15 M in 1). Isolated yields of 3 are reported. Er was determined by chiral stationary-phase high performance liquid chromatography (HPLC). [b] Benzylic chloride was used for 2 instead of benzylic bromide.

With conditions to generate each reactive intermediate independently at productive concentrations, we explored the scope of this transformation (Table 2, FIG. 3).

Reactions were performed at 0.4 mmol with 1 equiv of 1, 2 equiv of 2, 0.3 equiv base, 2 equiv CsF and 2 equiv crown ether in THF (0.15 M in 1). Isolated yields of 3 are reported. Er was determined by chiral stationary-phase high performance liquid chromatography (HPLC). [b] Benzylic chloride was used for 2 instead of benzylic bromide. Cinnamaldehyde derivatives bearing electron donating and electron withdrawing groups were well tolerated. (3a-3i). Aryl modifications on the aldehyde substrate did not impact yields or chemoselectivity substantially. The ability to employ either bromide or chloride leaving groups on 1 (Table 1, FIG. 2) allowed for the use of benzylic chloride o-QM precursors when the corresponding benzylic bromides were too unstable (e.g., 3k, 3n and 3o). For these cases, the corresponding benzyl chlorides can be successfully employed in the reaction and thus effectively expand the scope of the overall process.

Figure 4:
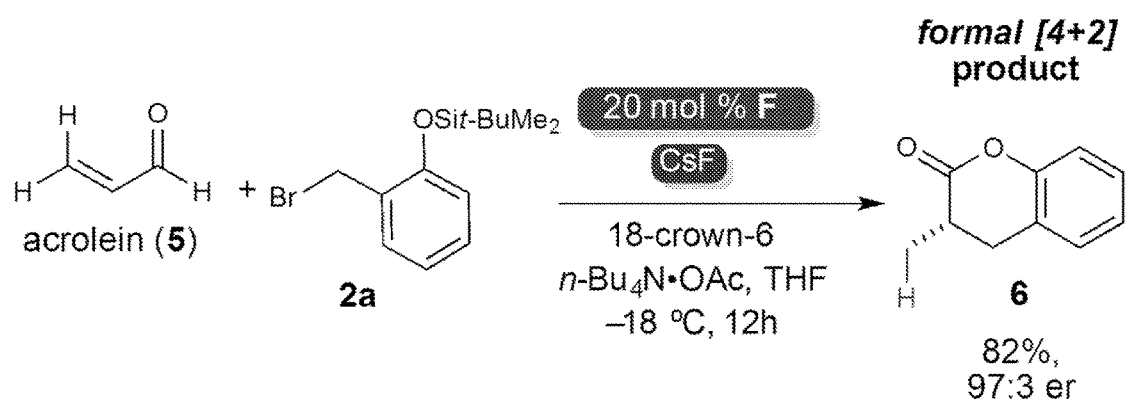
FIG. 4. Scheme 2. Formal [4+2] reaction with acrolein.

We also explored the scope of the o-QM precursor. A brief survey on the aromatic ring showed that yields were increased with electron donating groups (3j-3l). A current limitation that is not surprising is that electron withdrawing groups on the o-QM did not furnish any product (not shown). These groups presumably stabilize the resulting anionic phenoxide intermediate to the point where ejection of the bromide or chloride leaving group is not favored. The incorporation of additional substitution in the benzylic position of the o-bromo benzylphenol TBS ethers is possible (3m-3o) and extends the scope of the formal [4+3] process to include the generation of vicinal substituted products. The diastereoselectivity for these reactions is moderate, but this particular process is more challenging since β-substitution of α,β-unsaturated electrophiles (in this case, the o-QM) greatly slows down typical Michael/conjugate additions. With a highly reactive aldehyde like acrolein (5), the unexpected dihydrocoumarin 6 is obtained exclusively with enantioselectivity and excellent yield via Scheme 2 (FIG. 4), which is surprising giving the penchant for acrolein to oligomerize under typical nucleophilic conditions.[19]

Figure 5:
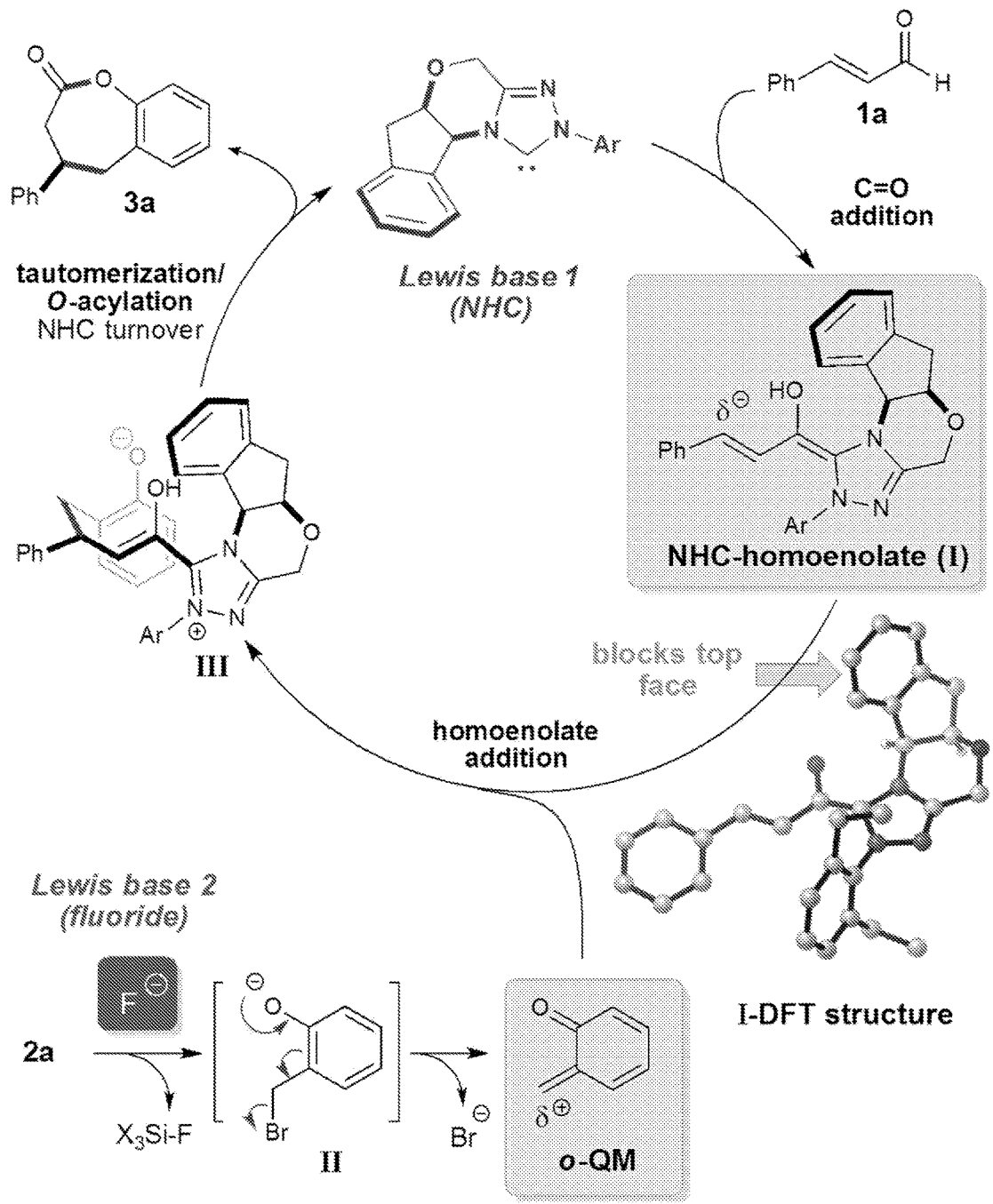
FIG. 5. Scheme 3. Reaction pathway.

Our current understanding of the pathway is shown in Scheme 3 (FIG. 5). The initial addition of the NHC (Lewis base 1) to the α,β-unsaturated aldehyde furnishes extended Breslow intermediate I after formal 1,2-hydrogen migration. The second Lewis base, fluoride ion, promotes generation of the o-QM electrophile from silylated phenol 2 via a desilylation/elimination cascade (2→II→o-QM). The pairing of the t-butyldimethyl silyl group and bromide leaving group produces the appropriate concentration of the sensitive o-QM for the desired transformation. Based on DFT calculations (B3LYP/6-31G*, gas phase), the NHC-homoenolate (I) exhibits a strong preference for reaction away from the more hindered face generated by the amino-indanol phenyl framework (I-DFT, as drawn). This nucleophile captures the transient o-QM through a carbon-carbon bond forming conjugate addition with what seems an open transition state. For o-QMs with β-substitution (leading to products 3m, 3n, and 3o), this leads to low levels of diasteromeric control. At this point in the cycle, intermediate III undergoes taumerization and intramolecular O-acylation of the phenoxide anion,[20] thereby releasing the carbene catalyst (C) and benzoxopinone product (3). The absolute stereochemistry of the product was confirmed by X-ray and then further assigned by analogy (see Supporting information). We attribute this difference in reactivity of acrolein (formal [4+2]) vs. the β-aryl substrates (formal [4+3]) to a fast protonation of this specific NHC-homoenolate intermediate. This protonated intermediate is an NHC-enolate equivalent that undergoes a subsequent Michael addition/O-acylation process similar to the catalytic cycle above, this time forming the observed six-membered ring.[21] The addition of a proton (H+) to the β-position is competitive if there is no aryl substitution in this location (e.g., acrolein, crotonaldehyde). However, this pathway is slower than C—C bond formation with the o-QM when a β-aryl substituent is present (e.g., cinnamaldehyde). Essentially, the fluoride ion, promotes generation of the o-QM electrophile from stability of the extended Breslow intermediate determines the fate of the nucleophilic NHC intermediate.

Our current understanding of the pathway is shown in Scheme 3 (FIG. 5). The initial addition of the NHC (Lewis base 1) to the α,β-unsaturated aldehyde furnishes extended Breslow intermediate I after formal 1,2-hydrogen migration. The second Lewis base, fluoride ion, promotes generation of the o-QM electrophile from silylated phenol 2 via a desilylation/elimination cascade (2→II→o-QM). The pairing of the t-butyldimethyl silyl group and bromide leaving group produces the appropriate concentration of the sensitive o-QM for the desired transformation. Based on DFT calculations (B3LYP/6-31G*, gas phase), the NHC-homoenolate (I) exhibits a strong preference for reaction away from the more hindered face generated by the amino-indanol phenyl framework (I-DFT, as drawn). This nucleophile captures the transient o-QM through a carbon-carbon bond forming conjugate addition with what seems an open transition state. For o-QMs with β-substitution (leading to products 3m, 3n, and 3o), this leads to low levels of diasteromeric control. At this point in the cycle, intermediate III undergoes taumerization and intramolecular O-acylation of the phenoxide anion,[20] thereby releasing the carbene catalyst (C) and benzoxopinone product (3). The absolute stereochemistry of the product was confirmed by X-ray and then further assigned by analogy (see Supporting information). We attribute this difference in reactivity of acrolein (formal [4+2]) vs. the β-aryl substrates (formal [4+3]) to a fast protonation of this specific NHC-homoenolate intermediate. This protonated intermediate is an NHC-enolate equivalent that undergoes a subsequent Michael addition/O-acylation process similar to the catalytic cycle above, this time forming the observed six-membered ring.[21] The addition of a proton (H+) to the β-position is competitive if there is no aryl substitution in this location (e.g., acrolein, crotonaldehyde). However, this pathway is slower than C—C bond formation with the o-QM when a β-aryl substituent is present (e.g., cinnamaldehyde). Essentially, the fluoride ion, promotes generation of the o-QM electrophile from stability of the extended Breslow intermediate determines the fate of the nucleophilic NHC intermediate.

Figure 6:
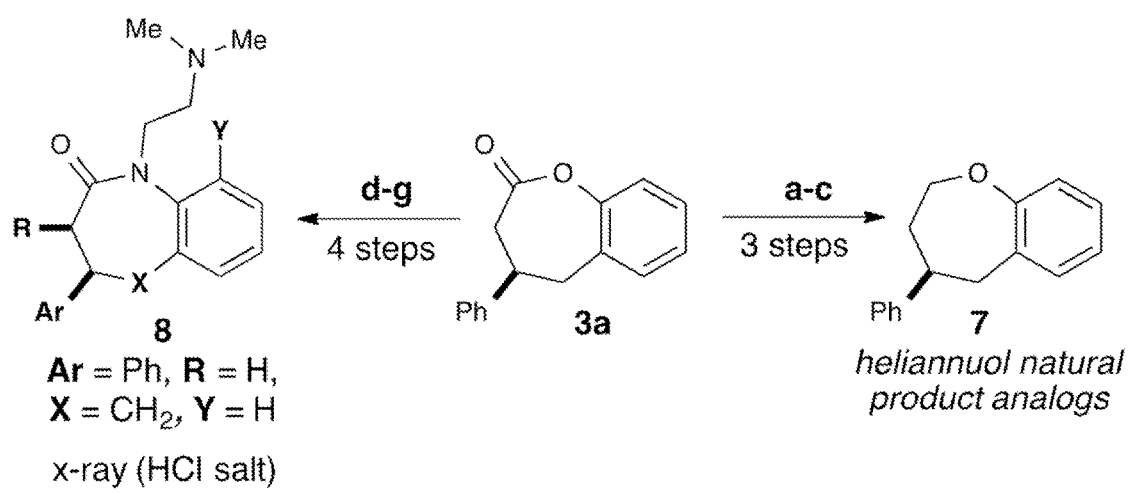
FIG. 6. Scheme 4. Synthesis of benzoxepanes and benzoazepinones[a]. [a] Reaction conditions: (a) $Me_2S$—$BH_3$, THF; 85%. (b) TsCl, $Et_3N$, $CH_2Cl_2$. (c) NaH, THF; 53% both steps. (d) $H_2SO_4$, MeOH; 74%. (e) $Tf_2O$, DCM; 99%. (f) $Pd(OAc)_2$, rac-BINAP, $Cs_2CO_3$, $H_2N(CH_2)_2N(CH_3)_2$, THF; 91%. (g) aq. LiOH, THF; then HBTU, i-Pr2EtN, DMF, 65% (as the HCl salt).
Figure 7:
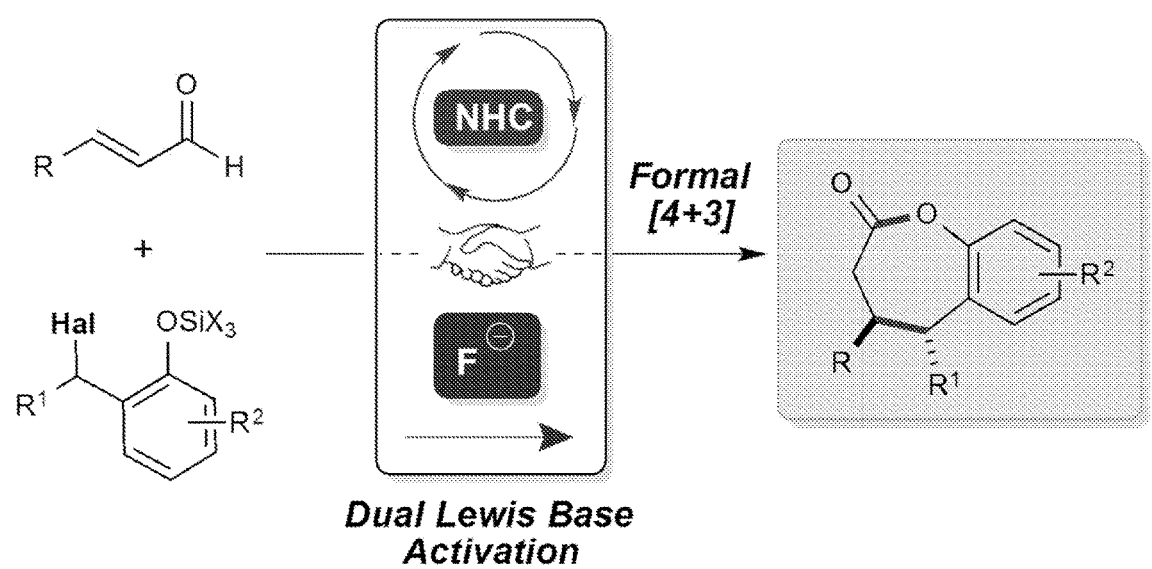
FIG. 7. Scheme 5. Dual Lewis Base Activation for Enantioselective [4+3] Heterocycloaddition.
Figure 8:
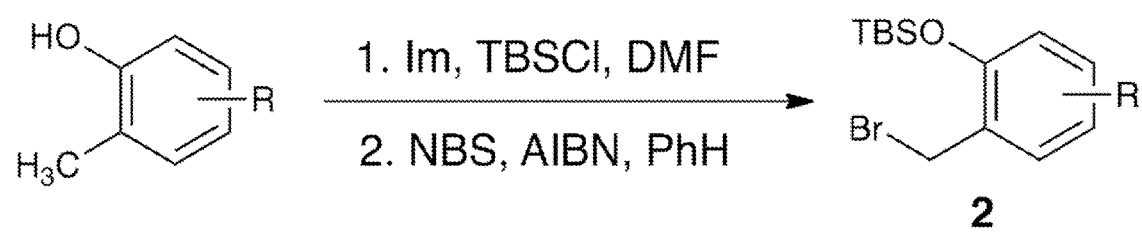
FIG. 8. General Procedure for the Synthesis of the Ortho Quinonemethides.
Figure 10:
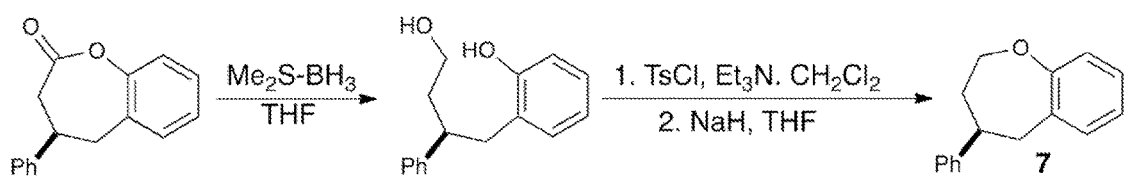
FIG. 10. General Procedure for synthetic transformations of benzoxopinones to benzoxepanes.
Figure 11:
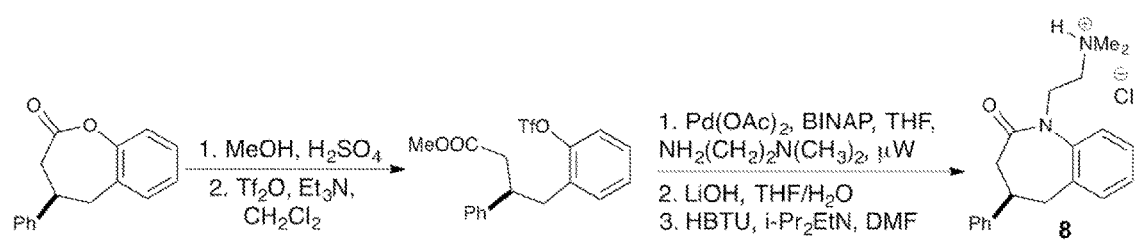
FIG. 11. General Procedure for synthetic transformations of benzoxopinones to benzoazepinones.

This process is a convergent, catalytic enantioselective route to these seven-membered ring lactones and enables rapid access to biologically relevant structures, including related benzoxepanes and benzoazepinones (Scheme 4, FIG. 6). Prior routes to these compounds are scarce and the dearth of convergent strategies to access them has presumably hampered investigation of their full potential. For example, benzoxopinone 3 was smoothly transformed into benzoxepane 7, which contains the core found in many compounds in the heliannuol family of natural products and could be utilized to access structural analogs.[22] In addition, the related benzoxepanes are known central nervous system depressants.[23] The overall replacement of the oxygen atom in 3a with a nitrogen substituent can be easily accomplished in four steps. This series of transformations accesses benzoazepinones which are related in structure to benzodiazepines drugs (e.g., Xanax, Valium)[24] by virtue of the seven-membered azepine structure fused to an aryl ring.[25]

Benzoazepinones with the same N,N-dimethylethyl side chain are related to the FDA-approved drug diltiazem,[26] a potent calcium channel blocker (Cardizem) and SQ 31,486, a candidate to reduce myocardial ischemia for cardioprotective treatments.[27]

This report highlights the new integration of two distinct Lewis base activation modes to discover an enantioselective organocatalytic formal [4+3]heterocycloaddition. The successful realization of this challenging "dual activation" concept has been achieved through concomitant in situ generation of two reactive, transient species: a nucleophilic NHC-homoenolate and a highly electrophilic ortho-quinone methide. In a broader strategic sense, the employment of a second Lewis base compatible with N-heterocyclic carbenes that accesses reactive electrophiles greatly expands the potential for new reaction discovery with these powerful organocatalysts.

Supplemental Experimental Information and Results

General Information

All reactions were carried out under a nitrogen atmosphere in oven-dried glassware with magnetic stirring. THF, diethyl ether, DMF, benzene, toluene, and dichloromethane were purified by passage through a bed of activated alumina. (See, Pangborn, A. B.; Giardello, M. A.; Grubbs, R. H.; Rosen, R. K.; Timmers F. J., *Organometallics* 1996, 15, 1518-1520.) Reagents were purified prior to use unless otherwise stated following the guidelines of Perrin and Armarego. (See, D. D. Perrin, W. L. Armarego, *Purification of Laboratory Chemicals;* 3rd Ed., Pergamon Press, Oxford. 1988). Purification of reaction products was carried out by flash chromatography using EM Reagent or Silicycle silica gel 60 (230-400 mesh). Analytical thin layer chromatography was performed on EM Reagent 0.25 mm silica gel 60-F plates. Visualization was accomplished with UV light and ceric ammonium nitrate stain, potassium permanganate stain or ninhydrin stain followed by heating. Infrared spectra were recorded on a Bruker Tensor 37 FT-IR spectrometer. $^1$H-NMR spectra were recorded on a Bruker Avance 500 MHz w/ direct cryoprobe (500 MHz) spectrometer and are reported in ppm using solvent as an internal standard (CDCl$_3$ at 7.26 ppm). Data are reported as (ap=apparent, s=singlet, d=doublet, t=triplet, q=quartet, m=multiplet, b=broad; coupling constant(s) in Hz, integration). Proton-decoupled $^{13}$C-NMR spectra were recorded on a Bruker Avance 500 MHz w/ direct cryoprobe (125 MHz) spectrometer and are reported in ppm using solvent as an internal standard (CDCl$_3$ at 77.05 ppm). Mass spectra data were obtained on a Waters Acquity Single Quadrupole ESI Spectrometer and Micromass Quadro II Spectrometer.

Trans-cinnamaldehyde and acrolein were obtained from commercial sources (Sigma Aldrich, Alfa Aesar). All other cinnamaldehyde derivatives were prepared according to literature procedures. (See, (a) Momose, Y.; Maekawa, T.; Yamano, T.; Kawada, M.; Odaka, H.; Ikeda, H.; Sohda, T. *J. Med. Chem.* 2002, 45, 1518. (b) Battistuzzi, G.; Cacchi, S.; Fabrizi, G. *Org. Len.* 2003, 5, 777. c) Noël, S.; Luo, C.; Pinel, C.; Djakovitch, L. *Adv. Synth. Catal.* 2007, 349, 1128). Ortho cresol derivatives, tert-butylchlorodimethylsilane used in the synthesis of the ortho quinonemethides precursors were obtained from commercial sources. Ortho quinonemethides 2d and 2e were synthesized following the experimental procedure previously reported in our group. (See, Mattson, A. E.; Scheidt, K. A. *J. Am. Chem. Soc.* 2007, 129, 4508).

Into an oven-dried 100 ml round bottom flask equipped with a magnetic stirbar, the o-cresol derivative (25 mmol, 1 equiv) was dissolved in DMF (25 ml). Then, tert-butyldimethylsilane chloride (27 mmol, 1.1 equiv) followed by imidazole (55 mmol, 2.2 equiv) were added in one portion. The reaction was purged with N$_2$ and stirred overnight under positive N$_2$ atmosphere. After 16 h stirring, the reaction was partitioned in 50 ml of water and 150 ml of EtOAc. The organic layer was separated, washed with 50 ml of water, dried over MgSO$_4$, filtrated and concentrated under reduced pressure. The oil obtained was repurified filtering it through a pad of SiO$_2$ using 1% EtOAc/hexanes. The oil obtained was introduced in a 100 ml round bottom flask equipped with a magnetic stir bar and a condenser. Then, the silylated phenol was dissolved in benzene (50 ml), and N-bromosuccinimide (25 mmol, 1 equiv) and AIBN (3.75 mmol, 0.15 equiv.) were added in one portion. The solution was purged with N$_2$ for 10 minutes and refluxed for 2 h. The reaction was allowed to cool to room temperature and was then filtered through a pad of SiO$_2$ using hexanes to furnish the benzyl bromide product 2 as a transparent liquid after concentration under reduced pressure.

(2-(bromomethyl)phenoxy)(tert-butyl)dimethylsilane (2a)

Prepared according to the general procedure using o-cresol. (6.9 g, 92% yield). Analytical data for 2a: $^1$H NMR (500 MHz, CDCl$_3$): δ 7.33 (dd, J=7.6, 1.7 Hz, 1H), 7.21-7.18 (m, 1H), 6.93 (dd, J=7.5, 1.0 Hz, 1H), 6.81 (dd, J=8.2, 0.8 Hz, 1H), 4.54 (s, 2H), 1.07-1.04 (s, 9H), 0.31-0.27 (s, 6H); $^{13}$C NMR (125 MHz, CDCl$_3$): δ 153.9, 131.2, 130.0, 128.4, 121.3, 118.7, 29.4, 25.8, 18.3, −4.1 ppm. IR (film) 2957, 2930, 2859, 1601, 1583, 1490, 1456, 1269, 926, 839, 826, 782, 755 cm$^{-1}$.

(2-(bromomethyl)-4-(tert-butyl)phenoxy)(tert-butyl)dimethylsilane (2b)

Prepared according to the general procedure using 4-(tert-butyl)-2-methylphenol. (7.9 g, 89%). Analytical data for 2b: $^1$H NMR (500 MHz, CDCl$_3$): δ 7.16=(d, J=2.6 Hz, 1H), 7.03 (dd, J=8.5, 2.6 Hz, 1H), 6.58 (d, J=8.5 Hz, 1H), 4.37 (s, 2H), 1.12 (d, J=3.4 Hz, 9H), 0.89 (s, 9H), 0.15-0.12 (m, 6H); $^{13}$C NMR (125 MHz, CDCl$_3$): δ 151.6, 143.9, 128.0, 127.4, 126.9, 117.9, 34.1, 31.5, 30.1, 25.8, 18.3, −4.1 ppm. IR (film) 2958, 2901, 2859, 1609, 1577, 1506, 1472, 1278, 1216, 1188, 1150, 1093, 944, 904, 862, 840, 821, 781, 675 cm$^{-1}$ (2-(1-bromoethyl)phenoxy)(tert-butyl)dimethylsilane (2c)

Prepared according to the general procedure using 2-ethylphenol. (7.3 g, 93%). Analytical data for 2c. $^1$H NMR (500 MHz, CDCl$_3$): δ 7.55 (dd, J=7.8, 1.7 Hz, 1H), 7.22-7.16 (m, 1H), 7.04-6.96 (m, 1H). 6.84-6.79 (m, 1H), 5.68 (q, J=7.0 Hz, 1H), 2.06 (d, J=7 Hz, 3H), 1.08 (s, 9H), 0.31 (d, J=20.0, 6H); $^{13}$C NMR (126 MHz, CDCl$_3$): δ 152.1, 133.6, 129.2, 127.5, 121.5, 118.6, 43.4, 25.9, 25.8, 25.4, 18.4, −4.1 ppm. IR (film) 2957, 2930, 2859, 1601, 1580, 1455, 1288, 1256, 1033, 919, 839, 824, 782, 754 cm$^{-1}$.

tert-butyl(2-(chloromethyl)-5-methoxyphenoxy)dimethylsilane (2d)

Prepared according the experimental procedure previously reported in our group. (See, Mattson, A. E.; Scheidt, K. A. *J. Am Chem. Soc.* 2007, 129, 4508). Analytical data for 2d. $^1$H NMR (500 MHz, CDCl$_3$): δ 7.26-7.25 (m, 1H), 6.52-6.50 (m, 1H), 6.39 (m, 1H), 4.60 (s, 2H), 3.79 (s, 3H), 1.05 (s, 9H), 0.29 (s, 6H). $^{13}$C NMR (125 MHz, CDCl3): δ 161.2, 155.2, 131.8, 121.1, 106.4, 105.6, 55.6, 42.3, 26.0, 25.9, 18.5 ppm. IR (film) 2956, 2932, 2858, 1611, 1505, 1260, 1202, 1166, 847 cm$^{-1}$.

tert-butyl(2-(chloromethyl)-5-methoxyphenoxy)dimethylsilane (2e)

To a ice bath cold solution of (2-((tert-butyldimethylsilyl) oxy)-5-methoxyphenyl)methanol (6.57 mmol, 1 equiv) in diethyl ether (17 ml) at 0° C. under positive N$_2$ atmosphere, PBr$_3$ (7.23 mmol, 1.1 equiv) was added dropwise. [1] The corresponding alcohol was synthesized following the same experimental procedure to obtain ortho quinonemethide precursor 2d. The solution stirred for 1 h in the ice bath and was partitioned in 10 ml of brine and 30 ml of diethyl ether. The organic layer was separated, dried over MgSO$_4$, filtered and concentrated under reduce pressure. The reddish oil obtained was filtered through a SiO$_2$ pad using 5-10% EtOAc/hexanes to obtain benzyl bromide 2e as a colorless oil (2.09 g, 96%). $^1$H NMR (500 MHz, CDCl$_3$): δ 6.90-6.86 (m, 1H), 6.74 (d, J=1.4 Hz, 2H), 4.50 (s, 2H), 3.76 (s, 3H), 1.04 (s, 9H), 0.25 (s, 6H); $^{13}$C NMR (125 MHz, CDCl$_3$): δ 153.7, 147.6, 128.8, 119.4, 115.8, 115.5, 55.7, 29.4, 25.8, 18.3, −4.1 ppm. IR (film) 2956, 2931, 2858, 1520, 1471, 1417, 1275, 1234, 1211, 1042, 905, 840, 781, 690 cm$^{-1}$.

Into a 25 ml round bottom flask, placed in an ice bath, 2-((tert-butyldimethylsilyl)oxy)benzaldehyde (2.75 mmol, 1 equiv) was dissolved in diethyl ether (1.5 ml) under positive N$_2$ atmosphere. 4-fluorophenethyl)magnesium bromide 2 M (1.4 ml, 1.1 equiv), prepared from the corresponding bromide in diethyl ether, was added dropwise in the reaction. The reaction stirred in the ice bath for 3 hours. The reaction was quenched adding 5 ml of NH$_4$Cl aqueous saturated solution. The slurry solution was extracted with diethyl ether (3×25 ml), dried over MgSO$_4$, filtrated and concentrated under vacuum pressure. The colorless oil obtained was purified through chromatography column using 5-20% EtOAc/hexanes to afford 1-(2-((tert-butyldimethylsilyl)oxy) phenyl)-3-(4-fluorophenyl)propan-1-ol as a white solid (595 mg. 84%). $^1$H NMR (500 MHz, CDCl$_3$): δ 7.37 (dd, J=7.6, 1.6 Hz, 1H), 7.18-7.11 (m, 3H), 7.00-6.92 (m, 3H), 6.79 (dd, J=8.1, 0.7 Hz, 1H), 4.97 (dt, J=8.8, 4.6 Hz, 1H), 2.88-2.78 (m, 1H), 2.69 (m, 1H), 2.11-1.96 (m, 2H), 0.99 (s, 9H), 0.24 (s, 6H); $^{13}$C NMR (125 MHz, CDCl$_3$): δ 152.6, 134.6, 129.9, 129.8, 128.2, 126.8, 121.3, 118.2, 115.2, 115.0, 69.0, 39.0, 31.6, 25.8, 18.2, −4.0, −4.1 ppm.

tert-butyl(2-(chloromethyl)-5-methoxyphenoxy)dimethylsilane (2f)

To a dry 100 mL round bottom flask under nitrogen, containing 1-(2-((tert-butyldimethylsilyl)oxy)phenyl)-3-(4-fluorophenyl)propan-1-ol (1.65 mmol, 1 equiv) was added toluene (16.5 mL). The reaction was cooled to 0° C. then freshly distilled thionyl chloride (4.95 mmol, 3 equiv) was added. The reaction was allowed to slowly attain room temperature and was stirred overnight. After 18 h the reaction was poured into 16 ml of 20% KOH. The layers were separated and the aqueous layer was extracted three times with CH$_2$Cl$_2$. The combined organics were dried with sodium sulfate, filtered and concentrated to yield 2f as a yellowish oil (605 mg, 97%) that was pure by $^1$H NMR. It was used in the next step without further purification. $^1$H NMR (500 MHz, CDCl$_3$): δ 7.54-7.45 (m, 1H), 7.22-7.11 (m, 3H), 7.03-6.92 (m, 3H), 6.79 (dd, J=8.1, 1.0 Hz, 1H), 5.30 (m, 1H), 2.89-2.80 (m, 1H), 2.80-2.69 (m, 1H), 2.46-2.36 (m, 1H), 2.30-2.19 (m, 1H), 0.95 (s, 9H), 0.21 (d, J=4.2 Hz, 6H); $^{13}$C NMR (125 MHz, CDCl$_3$): δ 152.3, 136.4, 136.4, 132.0, 130.1, 130.0, 129.1, 127.9, 121.5, 118.6, 115.3, 115.3, 115.2, 56.1, 40.3, 32.4, 25.7, −4.1, −4.3 ppm. IR (film) 2955, 2930, 2897, 2859, 1601, 1582, 1508, 1491, 1454, 1255, 1222, 921, 832, 782, 756 cm$^{-1}$.

tert-butyl((3-chloro-2,3-dihydro-1H-inden-4-yl)oxy) dimethylsilane (2g)

To a dry 100 mL round bottom flask under nitrogen, containing 7-((tert-butyldimethylsilyl)oxy)-2,3-dihydro-1H-inden-1-ol (3.10 mmol, 1 equiv) was added toluene (15 mL). The reaction was cooled to 0° C. then freshly distilled thionyl chloride (9.30 mmol, 3 equiv) was added. The reaction was allowed to slowly attain room temperature and stirred overnight. After 18 h the reaction was poured into 15 ml of 20% KOH. The layers were separated and the aqueous layer was extracted three times with CH$_2$Cl$_2$. The combined organics were dried with sodium sulfate, filtered and concentrated to yield 2g as a yellow oil (865 mg, 99%) that was pure by $^1$H NMR. It was used in the next step without further purification as 2g is acid sensitive and decomposes on the SiO$_2$ TLC plates. $^1$H NMR (500 MHz, CDCl$_3$): δ 6.96 (7, J=7.8 Hz, 1H), 6.66 (d, J=7.4 Hz, 1H), 6.44 (d, J=8 Hz, 1H), 5.32 (d, J=5.9 Hz, 1H), 3.12-3.00 (m, 1H), 2.66 (dd, J=16.0, 7.6, 1H), 2.33-2.12 (m, 2H). 0.84-0.81 (s, 9H), 0.09-0.03 (d, J=10.6 Hz, 6H); $^{13}$C NMR (125 MHz, CDCl$_3$): δ 152.3, 146.5, 130.7, 117.5, 116.5, 64.5, 37.0, 30.7, 25.4, −4.1, −4.3 ppm. IR (film) 2956, 2929, 2858, 1598, 1472, 1275, 1259, 1018, 852, 839, 780 cm$^{-1}$.

General Procedure for the Formal [4+3] Cycloaddition with Ortho Quinonemethides.

An oven-dried, screw-capped long reaction tube-vial equipped with a magnetic stirbar was taken into a nitrogen-filled drybox at which time tetrabutylammonium acetate (0.120 mmol, 0.30 equiv), cesium fluoride (0.800 mmol, 2 equiv), 18-crown ether-6 (0.800 mmol, 2 equiv), and azolium salt F (0.080 mmol, 0.20 equiv) were added. The vial was capped with a septum cap, removed from the drybox and put under positive N$_2$ pressure through a balloon. The long reaction tube-vial was cooled to −18° C. in a Cryocool at which time the cinnamaldehyde-derived enal (0.400 mmol, 1 equiv), was dissolved in THF (2.5 ml), was added. The ortho quinone methide precursor (0.800 mmol, 2 equiv), was dissolved in THF (2.5 ml) and added to the reaction via a syringe. The reaction was stirred at −18° C. for 12 h. (some reactions were detected to achieve full conversion before the 12 h reaction time by TLC analysis). The reaction mixture was filtered over a pad of silica gel washing with ethyl acetate and concentrated under reduced pressure. Purification by flash chromatography with EtOAc/hexanes afforded the corresponding lactones. The corresponding racemic compounds were prepared by employing the same protocol but with 3-mesityl-1-methyl-1H-benzo[d]imidazol-3-ium iodide (0.045 mmol, 0.20 equiv, azolium B) as the catalyst.

(R)-4-phenyl-4,5-dihydrobenzo[b]oxepin-2(3H)-one (3a)

Prepared according to the general procedure using cinnamaldehyde and (2-(bromomethyl)phenoxy)(tert-butyl)dimethylsilane (2a). The unpurified residue was purified by flash chromatography using hexanes with 1% to 5% of EtOAc/ hexanes to afford 3a as a colorless oil (61 mg, 64%). $^1$H NMR (500 MHz, CDCl$_3$): δ 7.26-7.19 (m, 3H), 7.18-7.13

(m, 1H), 7.14-7.03 (m, 5H), 3.54 (p, J=7.1 Hz, 1H), 3.11 (dd, J=14.1, 7.1 Hz, 1H), 2.82 (dd, J=14.1, 7.1 Hz, 1H), 2.67 (ddd, J=22.2, 12.6, 7.1, 2H); $^{13}$C NMR (125 MHz; CDCl$_3$): δ 170.4, 151.6, 143.3, 130.5, 128.8, 128.6, 127.2, 126.7, 125.8, 119.4, 44.3, 37.7, 36.5 ppm. IR (film) 3061, 3029, 2952, 2919, 1770, 1678, 1485, 1455, 1224, 1130, 1096, 980, 762, 700 cm$^{-1}$. LRMS (EI): Mass calcd for C$_{16}$H$_{14}$O$_2$[M]$^+$, 238.1. found 238.0. Enantiomeric ratio was measured by chiral phase HPLC (Chiralcel OD-H; 5% IPA/hexanes 1 mL/min, 210 nm), Rt$_1$ (major)=12.16 min, Rt$_2$ (minor) =15.33 min; er=96:4.

(R)-4-(p-tolyl)-4,5-dihydrobenzo[b]oxepin-2(3H)-one (3b)

Prepared according to the general procedure using (E)-3-(p-tolyl)acrylaldehyde and (2-(bromomethyl)phenoxy)(tert-butyl)dimethylsilane (2a). The unpurified residue was purified by flash chromatography using hexanes with 1% to 5% of EtOAc/hexanes to afford 3b as a colorless oil (59 mg, 59%). $^1$H NMR (500 MHz, CDCl$_3$): δ 7.34 (td, J=7.7, 1.7 Hz, 1H), 7.21-7.06 (m, 7H), 3.62 (m, 1H), 3.21 (dd, J=14.1, 7.1 Hz, 1H), 2.90 (dd, J=14.1, 6.7 Hz, 1H), 2.75 (dd, J=19.8, 12.5, 7.3, 2H), 2.34 (d, J=5.8 Hz, 3H); $^{13}$C NMR (125 MHz; CDCl$_3$): δ 170.6, 151.7, 140.4, 136.9, 130.6, 129.5, 128.9, 128.7, 126.6, 125.9, 119.5, 44.0, 37.9, 36.7, 21.0 ppm. IR (film)=3025, 2950, 2921, 2858, 1760, 1516, 1486, 1458, 1223, 1164, 1093, 1034, 963, 918, 745 cm$^{-1}$. LRMS (EI): Mass calcd for C$_{17}$H$_{16}$O$_2$[M]$^+$, 252.1. found 252.1. Enantiomeric ratio was measured by chiral phase HPLC (Chiralcel OD-H; 5% IPA/hexanes 1 mL/min, 210 nm), Rt$_1$ (major) =9.32 min, Rt$_2$ (minor)=12.32 min; er=98:2.

(R)-4-(m-tolyl)-4,5-dihydrobenzo[b]oxepin-2(3H)-one (3c)

Prepared according to the general procedure using (E)-3-(m-tolyl)acrylaldehyde and (2-(bromomethyl)phenoxy)(tert-butyl)dimethylsilane (2a). The unpurified residue was purified by flash chromatography using hexanes with 1% to 5% of EtOAc/hexanes to afford 3c as a colorless oil (58 mg, 57%). $^1$H NMR (500 MHz, CDCl$_3$): δ 7.34 (td, J=7.8, 1.7 Hz, 1H), 7.21-7.12 (m, 7H), 3.91 (p, J=7.2 Hz, 1H), 3.19 (dd, J=14.0, 7.15 Hz, 1H), 2.84 (dd, J=14.0, 6.6 Hz, 1H), 2.77-2.72 (m, 2H), 2.38 (s, 3H); $^{13}$C NMR (125 MHz; CDCl$_3$): δ 172.0, 158.8, 143.5, 136.6, 134.4, 130.8, 129.8, 128.9, 128.6, 127.0, 126.6, 125.7, 119.2, 39.2, 37.3, 35.5, 19.6 ppm. IR (film) 3023, 2953, 2927, 2856, 1758, 1487, 1458, 1221, 1184, 1133, 1096, 759 cm$^{-1}$. LRMS (EI): Mass calcd for C$_{17}$H$_{16}$O$_2$ [M]$^+$, 252.1. found 252.1. Enantiomeric ratio was measured by chiral phase HPLC (Chiralcel OD-H; 5% IPA/hexanes 1 mL/min, 210 nm), Rt$_1$ (major)=22.93 min, Rt$_2$ (minor)=46.40 min; er=98:2.

(R)-4-(3-bromophenyl)-4,5-dihydrobenzo[b]oxepin-2(3H)-one (3d)

Prepared according to the general procedure using (E)-3-(3-bromophenyl)acrylaldehyde and (2-(bromomethyl)phenoxy)(tert-butyl)dimethylsilane (2a). The unpurified residue was purified by flash chromatography using hexanes with 1% to 5% of EtOAc/hexanes to afford 3d as a colorless oil (71 mg, 56%). $^1$H NMR (500 MHz, CDCl$_3$): δ 7.43-7.39 (m, 1H), 7.38-7.33 (m, 2H), 7.24-7.14 (m, 6H), 3.60 (m, 1H), 3.21 (dd, J=14.1, 7.1 Hz, 1H), 2.90 (dd, J=14.1, 7.0 Hz, 1H), 2.75 (ddd, J=37.0, 12.6, 7.2 Hz, 2H); $^{13}$C NMR (125 MHz; CDCl$_3$): δ 170.2, 151.7, 145.5, 130.5, 130.5, 130.5, 130.1, 129.0, 128.4, 126.1, 125.3, 122.8, 119.6, 44.0, 37.6, 36.4 ppm. IR (film) 2954, 2924, 2854, 1760, 1679, 1609, 1584, 1487, 1457, 1224, 1182, 1129, 1097, 1049, 782, 762, 701 cm$^{-1}$. LRMS (EI): Mass calcd for C$_{16}$H$_{13}$BrO$_2$ [M]$^+$, 316.0. found 316.0. Enantiomeric ratio was measured by chiral phase HPLC (Chiralcel AD-H; 5% IPA/hexanes 0.5 mL/min, 210 nm), Rt$_1$ (major)=10.66 min, Rt$_2$ (minor) =11.98 min; er=99:1.

(R)-4-(3-methoxyphenyl)-4,5-dihydrobenzo[b]oxepin-2(3H)-one (3e)

Prepared according to the general procedure using (E)-3-(3-methoxyphenyl)acrylaldehyde and (2-(bromomethyl)phenoxy)(tert-butyl)dimethylsilane (2a). The unpurified residue was purified by flash chromatography using hexanes with 1% to 5% of EtOAc/hexanes to afford 3e as a colorless oil (60 mg, 56%). $^1$H NMR (500 MHz, CDCl$_3$): δ 7.36-7.31 (m, 1H), 7.26-7.13 (m, 4H), 6.82-6.77 (m, 2H), 6.77-6.74 (m, 1H), 3.78 (s, 3H), 3.62 (p, J=7.1 Hz, 1H), 3.22 (dd. J=14.1, 7.2 Hz, 1H), 2.92 (dd, J=14.1, 6.6 Hz, 1H), 2.81-2.71 (m, 2H); $^{13}$C NMR (125 MHz, CDCl$_3$): δ 170.6, 159.9, 151.7, 145.0, 130.6, 129.9, 128.9, 128.8, 125.9, 119.6, 119.0, 112.5, 112.5, 55.2, 44.4, 37.8, 36.5 cm$^{-1}$. IR (film) 2955, 2923, 2852, 1760, 1487, 1458, 1224, 1206, 1183, 1133, 782, 759, 695 cm$^{-1}$. LRMS (EI): Mass calcd for C$_{17}$H$_{16}$O$_3$[M]$^+$, 268.1. found 268.1; Enantiomeric ratio was measured by chiral phase HPLC (Chiralcel OD-H; 1% IPA/hexanes 1 mL/min, 210 nm), Rt$_1$ (major)=33.45 min, Rt$_2$ (minor)=38.35 min; er=99:1.

(R)-4-(4-bromophenyl)-4,5-dihydrobenzo[b]oxepin-2(3H)-one (3f)

Prepared according to the general procedure using (E)-3-(4-bromophenyl)acrylaldehyde and (2-(bromomethyl)phenoxy)(tert-butyl)dimethylsilane (2a). The unpurified residue was purified by flash chromatography using hexanes with 1% to 5% of EtOAc/hexanes to afford 3f as a colorless oil (77 mg, 61%). $^1$H NMR (500 MHz, CDCl$_3$): δ 7.44 (d, J=8.4 Hz, 1H), 7.35 (td, J=7.8, 1.6 Hz, 1H), 7.22-7.13 (m, 2H), 7.09 (d, J=8.4 Hz, 2H), 3.61 (q, J=7.1 Hz, 1H), 3.19 (dd, J=14.1, 7.1 Hz, 1H), 2.87 (dt, J=14.1, 7.25 Hz, 1H), 2.78 (dd, J=7.5, 12.6, 1H), 2.70 (dd, J=7.0, 12.6, 1H); $^{13}$C NMR (125 MHz; CDCl$_3$): δ 170.2, 151.7, 142.3, 132.0, 130.5, 128.9, 128.5, 126.0, 121.2, 119.6, 43.9, 37.6, 36.5 ppm. IR (film) 2950, 2924, 2853, 1733, 1678, 1584, 1487, 1456, 1223, 1181, 1130, 1093, 1072, 1010, 755 cm$^{-1}$. LRMS (EI): Mass calcd for C$_{16}$H$_{13}$BrO$_2$ [M]$^+$, 316.0. found 316.1. Enantiomeric ratio was measured by chiral phase HPLC (Chiralcel OD-H; 5% IPA/hexanes 1 mL/min, 210 nm), Rt$_1$ (major) =12.25 min, Rt$_2$ (minor)=22.52 min; er=96:4.

(R)-4-(naphthalen-1-yl)-4,5-dihydrobenzo[b]oxepin-2(3H)-one (3g)

Prepared according to the general procedure using (E)-3-(naphthalen-1-yl)acrylaldehyde and (2-(bromomethyl)phenoxy)(tert-butyl)dimethylsilane (2a). The unpurified residue was purified by flash chromatography using hexanes with 1% to 5% of EtOAc/hexanes to afford 3g as a colorless oil (71 mg, 62%). $^1$H NMR (500 MHz, CDCl$_3$): δ 7.91 (d, J=8.5 Hz, 1H), 7.74 (t, J=7.9 Hz, 1H), 7.63 (dq, J=7.0, 3.7 Hz, 1H), 7.43 (ddd, J=8.4, 6.9, 1.3 Hz, 1H), 7.37 (dt, J=13.2, 3.2 Hz, 1H), 7.29-7.25 (m, 2H), 7.20 (tt, J=9.8, 4.9 Hz, 1H), 7.03 (dd, J=10.4, 4.3 Hz, 2H), 6.99-6.94 (m, 1H), 4.38 (p, J=7.1 Hz, 1H), 3.22 (dd, J=14.0, 7.1 Hz, 1H), 2.87 (dt, J=14.0, 7.0

Hz, 1H), 2.81-2.70 (m, 2H); $^{13}$C NMR (125 MHz; CDCl$_3$): δ 170.9, 151.8, 138.4, 134.1, 130.6, 130.5, 129.3, 129.0, 128.8, 127.8, 126.6, 125.9, 125.8, 125.5, 122.9, 122.3, 119.5, 38.7, 37.1, 35.8 ppm. IR (film) 3059, 2955, 2925, 1757, 1486, 1398, 1223, 1183, 1135, 1099, 797, 761, 736 cm$^{-1}$. LRMS (EI): Mass calcd for C$_{20}$H$_{16}$O$_2$[M]$^+$, 288.1. found 288.1. Enantiomeric ratio was measured by chiral phase HPLC (Chiralcel OD-H; 5% IPA/hexanes 1 mL/min, 210 nm), Rt$_1$ (major)=28.16 min, Rt$_2$ (minor)=36.94 min; er=95:5.

(R)-4-(naphthalen-2-yl)-4,5-dihydrobenzo[b]oxepin-2(3H)-one (3h)

Prepared according to the general procedure using (E)-3-(naphthalen-2-yl)acrylaldehyde and (2-(bromomethyl)phenoxy)(tert-butyl)dimethylsilane (2a). The unpurified residue was purified by flash chromatography using hexanes with 1% to 5% of EtOAc/hexanes to afford 3h as a colorless oil (77 mg, 67%). $^1$H NMR (500 MHz, CDCl$_3$): δ 7.86-7.76 (m, 3H), 7.66 (d, J=6.0 Hz, 1H), 7.52-7.44 (m, 2H), 7.40-7.31 (m, 2H), 7.24-7.15 (m, 3H), 3.83 (p, J=7.1 Hz, 1H), 3.31 (dd, J=14.1, 7.2 Hz, 1H), 3.03 (td, J=14.1, 6.1 Hz, 1H), 2.88 (dd, J=7.3, 1.6 Hz, 2H). $^{13}$C NMR (125 MHz; CDCl$_3$): δ 170.6, 151.8, 140.7, 133.4, 132.6, 130.6, 128.8, 128.8, 128.7, 127.9, 127.6, 126.4, 126.0, 125.2, 125.1, 119.6, 44.5, 37.7, 36.6 ppm. IR (film) 2954, 2924, 2854, 1764, 1508, 1486, 1458, 1224, 1183, 1133, 1094, 981, 819, 760 cm$^1$. LRMS (EI): Mass calcd for C$_{20}$H$_{16}$O$_2$[M]$^+$, 288.1. found 288.0. Enantiomeric ratio was measured by chiral phase HPLC (Chiralcel OD-H; 5% IPA/hexanes 1 mL/min, 210 nm), Rt$_1$ (major)=18.82 min, Rt$_2$ (minor)=24.55 min; er=96:4.

(R)-4-(4-chlorophenyl)-4,5-dihydrobenzo[b]oxepin-2(3H)-one (3i)

Prepared according to the general procedure using (E)-3-(4-chlorophenyl)acrylaldehyde and (2-(bromomethyl)phenoxy)(tert-butyl)dimethylsilane (2a). The unpurified residue was purified by flash chromatography using hexanes with 1% to 5% of EtOAc/hexanes to afford 3l as a colorless oil (70 mg, 64%). $^1$H NMR (500 MHz, CDCl$_3$): δ 7.28 (m, 1H), 7.25-7.20 (m, 2H), 7.15-7.06 (m, 5H), 3.56 (p, J=7.1 Hz, 1H), 3.13 (dd, J=14.1, 7.1 Hz, 1H), 2.81 (dd, J=14.1, 7.0 Hz, 1H), 2.72 (dd, J=12.6, 7.4 Hz, 1H), 2.63 (dd, J=12.6, 6.9 Hz, 1H); $^{13}$C NMR (125 MHz; CDCl$_3$): δ 170.3, 151.7, 141.7, 133.1, 130.5, 129.0, 128.9, 128.5, 128.2, 126.0, 119.6, 43.8, 37.7, 36.6 ppm. IR (film) 3064, 2920, 2855, 1760, 1583, 1494, 1223, 1182, 1131, 1093, 1014, 759 cm$^{-1}$. LRMS (EI): Mass calcd for C$_{16}$H$_{13}$ClO$_2$ [M]$^+$, 272.1. found 272.0; Enantiomeric ratio was measured by chiral phase HPLC (Chiralcel OD-H; 5% IPA/hexanes 1 mL/min, 210 nm), Rt$_1$ (major)=21.56 min, Rt$_2$ (minor)=37.04 min; er=96:4.

(R)-7-(tert-butyl)-4-phenyl-4,5-dihydrobenzo[b]oxepin-2(3H)-one (3j)

Prepared according to the general procedure using cinnamaldehyde and (2-(bromomethyl)-4-(tert-butyl)phenoxy)(tert-butyl)dimethylsilane (2b). The unpurified residue was purified by flash chromatography using hexanes with 1% to 5% of EtOAc/hexanes to afford 3j as a colorless oil (75 mg, 64%). $^1$H NMR (500 MHz, CDCl$_3$): δ 7.31-7.21 (m, 2H), 7.19 (m, 2H), 7.13 (dd, J=7.2, 5.8 Hz, 2H), 7.06 (d, J=2.3 Hz, 1H), 7.00 (d, J=8.4 Hz, 1H), 3.57 (p, J=7.1 Hz, 1H), 3.13 (dd, J=14.0, 7.1 Hz, 1H), 2.80 (dd, J=14.0, 6.7 Hz, 1H), 2.69 (ddd, J=12.6, 7.4, 7.1 Hz, 2H), 1.24 (s, 9H); $^{13}$C NMR (125 MHz; CDCl$_3$): δ 171.0, 149.4, 148.9, 143.5, 128.8, 128.1, 127.7, 127.3, 126.8, 125.3, 118.8, 44.5, 37.8, 37.0, 34.5, 31.4 ppm. IR (film) 3062, 2962, 1758, 1496, 1454, 1227, 1183, 1136, 1112, 1099, 1079, 759, 715, 700 cm$^{-1}$. LRMS (EI): Mass calcd for C$_{20}$H$_{22}$O$_2$ [M]$^+$, 294.2. found 294.1; Enantiomeric ratio was measured by chiral phase HPLC (Chiralcel OD-H; 5% IPA/hexanes 1 mL/min, 210 nm), Rt$_1$ (major)=8.76 min, Rt$_2$ (minor)=7.77 min; er=98:2.

(R)-8-methoxy-4-phenyl-4,5-dihydrobenzo[b]oxepin-2(3H)-one (3k)

Prepared according to the general procedure using cinnamaldehyde and tert-butyl(2-(chloromethyl)-5-methoxyphenoxy)dimethylsilane (2d). The unpurified residue was purified by flash chromatography using hexanes with 1% to 5% of EtOAc/hexanes to afford 3k as a colorless oil (73 mg, 68%). $^1$H NMR (500 MHz, CDCl$_3$): δ 7.15-7.08 (m, 2H), 7.09-7.03 (m, 1H), 7.02-6.95 (m, 2H), 6.87-6.82 (m, 1H), 6.57-6.50 (m, 2H), 3.63 (s, 3H), 3.42 (p, J=7.1 Hz, 1H), 2.97 (dd, J=14.3, 7.1 Hz, 1H), 2.68-2.60 (dd, J=14.3, 6.5, 1H), 2.60-2.51 (ddd, J=12.5, 7.4, 7.3, 2H); $^{13}$C NMR (125 MHz; CDCl$_3$): δ 170.6, 159.9, 152.3, 143.5, 130.9, 128.8, 127.2, 126.7, 120.7, 111.3, 105.5, 55.6, 44.7, 37.9, 35.8 ppm. IR (film) 3029, 3003, 2950, 2834, 1763, 1620, 1505, 1464, 1271, 1230, 1154, 1103, 1032, 758, 701 cm$^{-1}$. LRMS (EI): Mass calcd for [C$_{17}$H$_{17}$O$_3$]$^+$ [M+H]$^+$, 269.1. found 269.3. Enantiomeric ratio was measured by chiral phase HPLC (Chiralcel AD-H; 2% IPA/hexanes 1 mL/min, 210 nm), Rt$_1$ (major)=35.45 min, Rt$_2$ (minor)=49.42 min; er=99:1.

(R)-7-methoxy-4-phenyl-4,5-dihydrobenzo[b]oxepin-2(3H)-one (3l)

Prepared according to the general procedure using cinnamaldehyde and ((2-(bromomethyl)-4-methoxyphenoxy)(tert-butyl)dimethylsilane (2e). The unpurified residue was purified by flash chromatography using hexanes with 1% to 5% of EtOAc/hexanes to afford 3l as a colorless oil (69 mg, 64%). $^1$H NMR (500 MHz, CDCl$_3$): δ 7.26 (m, 2H), 7.22-7.17 (m, 1H), 7.15 (m, 2H), 7.01 (d, J=8.8 Hz, 1H), 6.76 (dd, J=8.8, 3.0 Hz, 1H), 6.62 (d, J=3.0 Hz, 1H), 3.73 (s, 3H), 3.60-3.52 (m, 2H), 3.10 (dd, J=14.0, 7.2 Hz, 1H), 2.86-2.77 (dd, J=14.0, 6.8 Hz, 1H), 2.70 (ddd, J=12.5, 7.4, 7.1 Hz, 2H); $^{13}$C NMR (125 MHz; CDCl$_3$): δ 171.1, 157.1, 145.4, 143.4, 130.0, 128.9, 127.3, 126.8, 120.3, 115.8, 113.0, 55.7, 44.2, 37.7, 36.8 ppm. IR (film) 3029, 3003, 2955, 2837, 1748, 1677, 1588, 1493, 1454, 1431, 1234, 1156, 1131, 981, 883, 701 cm$^{-1}$. LRMS (ESI): Mass calcd for [C$_{17}$H$_{17}$O$_3$]$^+$ [M+H]$^+$, 269.1. found 269.3. Enantiomeric ratio was measured by chiral phase (Chiralcel OD-H; 5% IPA/hexanes 1 mL/min, 210 nm), Rt$_1$ (minor)=24.55 min, Rt$_2$ (major)=15.69 min; er=99:1.

(4S,5R)-5-methyl-4-phenyl-4,5-dihydrobenzo[b]oxepin-2(3H)-one and (4R,5R)-5-methyl-4-phenyl-4,5-dihydrobenzo[b]oxepin-2(3H)-one (syn) (3m)

Prepared according to the general procedure using cinnamaldehyde and (2-(bromomethyl)-4-methoxyphenoxy)(tert-butyl)dimethylsilane (2c). The unpurified residue was purified by flash chromatography using hexanes with 1% to 5% of EtOAc/hexanes to afford 3m as a colorless oil (83 mg, 83%). Both diastereoisomers were inseparable by flash chromatography column. HPLC. $^1$H NMR (500 MHz, CDCl$_3$): δ 7.33-7.10 (m, 7H), 7.08 (d, J=8.0 Hz, 1H), 6.72 (m, 1H), 3.34-3.21 (m, 1H), 2.96-2.88 (m, 1H), 2.76 (dd, J=12.7, 8.4 Hz, 1H), 2.44 (dd, J=12.7, 2.6 Hz, 1H), 1.15 (t, J=6.9 Hz, 3H); $^{13}$C NMR (125 MHz, CDCl$_3$): δ 170.6, 151.5, 143.3, 134.1 128.9, 128.3, 127.4, 127.1, 126.1, 119.5, 52.3, 38.6, 38.1, 16.8 ppm. IR (film) 3063, 3032, 2969, 2935, 2879, 1766, 1606, 1582, 1485, 1453, 1217, 1137, 1117, 1096, 955, 763, 701 cm$^{-1}$. LRMS (EI): Mass calcd for C$_{17}$H$_{16}$O$_2$[M]$^+$, 252.1. found 252.1. Enantiomeric ratio was measured by chiral phase HPLC: (anti) (Chiralcel AD-H; 2% IPA/hexanes 0.5 mL/min, 210 nm) Rt$_1$ (min)=8.29 min, Rt$_2$ (major)=9.92 min; er=91:9.

(4S,5R)-5-(4-fluorophenethyl)-4-phenyl-4,5-dihydrobenzo[b]oxepin-2(3H)-one (3n)

Prepared according to the general procedure using cinnamaldehyde and tert-butyl(2-(1-chloro-3-(4-fluorophenyl)propyl)phenoxy)dimethylsilane (2f). The unpurified residue was purified by flash chromatography using hexanes with 1% to 5% of EtOAc/hexanes to afford 3n as a colorless oil (122 mg, 85%). The diastereomers were separated by preparative HPLC.

Analytical data for 3n:
(4S,5R)-5-(4-fluorophenethyl)-4-phenyl-4,5-dihydrobenzo[b]oxepin-2(3H)-one: $^1$H NMR (500 MHz, CDCl$_3$): δ 7.43-7.36 (m, 1H), 7.33-7.19 (m, 6H), 7.09 (t, J=8.9 Hz, 1H), 7.00-6.83 (m, 5H), 3.76-3.64 (m, 1H), 3.50-3.37 (m, 1H), 2.79-2.66 (m, 2H), 2.66-2.51 (m, 2H), 1.73-1.58 (m, 2H); $^{13}$C NMR (125 MHz, CDCl$_3$): δ 170.6, 162.3, 160.3, 151.9, 138.8, 137.1, 130.2, 129.6, 129.6, 129.0, 128.6, 128.5, 128.1, 127.9, 127.7, 127.4, 126.7, 126.1, 125.9, 48.3, 40.1, 39.5, 32.7, 31.5 ppm. IR (film) (mixture diastereoisomers) 3034, 2928, 2865, 1761, 1602, 1509, 1485, 1453, 1219, 1131, 1106, 826, 759, 702 cm$^{-1}$. LRMS (EI): Mass calcd for C$_{24}$H$_{21}$FO$_2$ [M]$^+$, 360.2. found 360.1; Enantiomeric ratio was measured by chiral phase HPLC (Chiralcel AD-H; 3% IPA/hexanes 0.5 mL/min, 210 nm), Rt$_1$ (minor)=16.90 min, Rt$_2$ (major)=17.79 min; er=89:11.

(4R,5R)-5-(4-fluorophenethyl)-4-phenyl-4,5-dihydrobenzo[b]oxepin-2(3H)-one: $^1$H NMR (500 MHz, CDCl$_3$): δ 7.43-7.34 (m, 1H), 7.34-7.17 (m, 5H), 7.10 (d, J=7.0 Hz, 2H), 6.97-6.85 (m, 5H), 3.23 (m, 1H), 3.16-3.04 (m, 1H), 2.75-2.56 (m, 2H), 2.55-2.43 (m, 1H), 2.43-2.31 (m, 1H), 2.26-2.11 (m, 1H), 1.90 (m, 1H); $^{13}$C NMR (125 MHz, CDCl$_3$): δ 170.4, 162.3, 160.3, 151.8, 143.7, 136.8, 131.4, 129.7, 129.6, 129.0, 128.7, 127.4, 126.7, 126.2, 120.5, 115.2, 115.0, 50.7, 46.0, 38.5, 33.7, 33.0 ppm. IR (film) (mixture diastereoisomers) 3034, 2928, 2865, 1761, 1602, 1509, 1485, 1453, 1219, 1131, 1106, 826, 759, 702 cm$^{-1}$. LRMS (ET): Mass calcd for C$_{24}$H$_{21}$FO$_2$ [M]$^+$, 360.2. found 360.1; Enantiomeric ratio was measured by chiral phase HPLC (Chiralcel AD-H; 3% IPA/hexanes 0.5 mL/min, 210 nm), Rt$_1$ (major)=25.08, Rt$_2$ (minor)=32.65 min; er=68:32.

(4S,4aR)-4-phenyl-4,4a,5,6-tetrahydroindeno[7,1-bc]oxepin-2(3H)-one (3o)

Prepared according to the general procedure using cinnamaldehyde and (tert-butyl((3-chloro-2,3-dihydro-1H-inden-4-yl)oxy)dimethylsilane (2g). The unpurified residue was purified by flash chromatography using hexanes with 1% to 5% of EtOAc/hexanes to afford 3o as a colorless oil (83 mg, 79%). The diastereomers were separated by preparative HPLC.

Analytical data for 3o:
(4S,4aR)-4-phenyl-4,4a,5,6-tetrahydroindeno[7,1-bc]oxepin-2(3H)-one: $^1$H NMR (500 MHz, CDCl$_3$): δ 7.35-7.22 (m, 4H), 7.10-7.05 (d, J=7.5 Hz, 1H), 7.02 (d, J=8.0 Hz, 1H), 6.89 (dd, J=7.5, 1.6 Hz, 2H), 3.95 (t, J=9.0 Hz, 1H), 3.83 (m, 1H), 2.99 (dd, J=20.1, 8.1 Hz, 1H), 2.81 (dd, J=12.2, 6.3 Hz, 1H), 2.73-2.63 (m, 1H), 2.34-2.23 (m, 1H), 2.21-2.08 (m, 1H), 1.67-1.59 (m, 1H); $^{13}$C NMR (125 MHz, CDCl$_3$): δ 170.8, 149.2, 146.7, 140.5, 133.4, 129.4, 128.5, 127.9, 127.6, 121.7, 115.9, 49.3, 44.6, 40.0, 32.5, 26.8 ppm. IR (film) (mixture diastereoisomers) 3029, 2941, 2849, 1761, 1589, 1493, 1231, 1118, 774, 763, 701 cm$^1$. LRMS (EI): Mass calcd for C$_{18}$H$_{16}$O$_2$[M]$^+$, 264.1. found 264.1; Enantiomeric ratio was measured by chiral phase HPLC (Chiralcel AD-H; 6% IPA/hexanes 1 mL/min, 210 nm), Rt$_1$ (minor)=13.86, Rt$_2$ (major)=15.38 min; er=87:13.

(4R,4aR)-4-phenyl-4,4a,5,6-tetrahydroindeno[7,1-bc]oxepin-2(3H)-one: $^1$H NMR (500 MHz, CDCl$_3$): δ 7.42-7.34 (m, 4H), 7.32-7.23 (m, 2H), 7.11 (d, J=7.5 Hz, 1H), 6.94 (d, J=8.0, 1H), 3.68 (t, J=9.6 Hz, 1H), 3.28-3.11 (m, 2H), 3.04-2.94 (m, 2H), 2.64 (dt, J=12.8, 1.1, 1H), 2.22-2.09 (m, 1H), 1.90 (m, 1H); $^{13}$C NMR (125 MHz, CDCl$_3$): δ 171.2, 149.1, 145.6, 143.6, 134.8, 129.3, 128.9, 127.5, 127.3, 121.7, 116.1, 51.1, 47.6, 39.7, 31.3, 28.7 ppm. IR (film) (mixture diastereoisomers) 3029, 2941, 2849, 1761, 1589, 1493, 1231, 1118, 774, 763, 701 cm$^{-1}$. LRMS (EI): Mass calcd for C$_{18}$H$_{16}$O$_2$ [M]$^+$, 264.1. found 264.1; Enantiomeric ratio was measured by chiral phase HPLC (Chiralcel AD-H; 6% IPA/hexanes 1 mL/min, 210 nm), Rt$_1$ (major)=23.38, Rt$_2$ (minor)=34.38 min; er=56:44.

3-methylchroman-2-one (6)

Prepared according to the general procedure using acrolein (5) and (2-(bromomethyl)phenoxy)(tert-butyl)dimethylsilane (2a). The unpurified residue was purified by flash chromatography using hexanes with 1% to 5% of EtOAc/hexanes to afford 6 as a white solid (53 mg, 82%). $^1$H NMR (500 MHz, CDCl$_3$): δ 7.27-7.22 (m, 1H), 7.17 (d, J=7.5 Hz, 1H), 7.11-7.06 (m, 1H), 7.03 (dd, J=8.1, 0.7 Hz, 1H), 2.97 (dd, J=14.5, 5.1 Hz, 1H), 2.87-2.73 (m, 2H), 1.37 (d, J=6.5 Hz, 3H); $^{13}$C NMR (125 MHz, CDCl$_3$): δ 171.7, 151.8, 128.2, 128.0, 124.3, 122.9, 116.6, 34.2, 31.7, 15.4. IR (film) 2974, 2936, 2876, 1766, 1615, 1590, 1489, 1460, 1357, 1230, 1146, 1086, 1039, 935, 759. cm$^{-1}$. LRMS (GCMS): Mass calcd for C$_{10}$H$_{10}$O$_2$ [M]$^+$, 162.1. found 162.0; Enantiomeric ratio was measured by chiral phase HPLC (Chiralcel AD-H; 5% IPA/hexanes 0.5 mL/min, 210 nm), Rt$_1$ (major)=20.28, Rt$_2$ (minor)=17.25 min; er=97:3.

Into a cold ice bath solution of lactone 3a (0.21 mmol, 1 equiv) in THF (1 ml) under N$_2$ positive atmosphere, BH$_3$-Me$_2$S (0.21 mmol, 1 equiv) complex 2 M in THF was added dropwise. The reaction was allowed to achieve room temperature and it stirred overnight. After 16 hours, the reaction was quenched by adding 2 ml of aqueous saturated NH$_4$Cl solution and it was extracted with CH$_2$Cl$_2$ (3×10 ml). The combined organic layers were dried over MgSO$_4$, filtrated and concentrated under vacuum pressure. The resulting residue was purified by flash column chromatography on silica gel using 1 to 10% EtOAc/hexanes to afford a yellowish oil in 85% yield (43 mg). $^1$H NMR (500 MHz, CDCl$_3$): δ 7.33-7.27 (m, 2H), 7.26-7.15 (m, 2H), 7.07 (tt, J=10.5, 5.3 Hz, 1H), 6.84 (dd, J=7.4, 1.5 Hz, 1H), 6.81-6.73 (m, 2H), 3.72 (dt, J=10.9, 6.2 Hz, 1H), 3.62 (dt, J=10.7, 6.3 Hz, 1H), 3.20-3.06 (m, 2H), 2.88-2.76 (m, 1H), 2.03-1.93 (m, 2H); $^{13}$C NMR (125 MHz, CDCl$_3$): δ 154.0, 144.7, 131.3, 128.5, 127.7, 127.5, 126.5, 126.4, 120.3, 115.8, 61.3, 43.4, 37.3, 36.9 ppm.

4-phenyl-2,3,4,5-tetrahydrobenzo[b]oxepine (7)

Into a solution of the phenol alcohol (0.18 mmol, 1 equiv) and tosyl chloride (0.18 mmol, 1 equiv) in 1 ml of CH$_2$C$_2$ under positive $N_2$ atmosphere, $Et_3N$ (0.27 mmol, 1.5 equiv) was added dropwise and the reaction stirred for 40 hours at room temperature. TLC showed starting material consumption, therefore the reaction was partitioned in 5 ml of water and 20 ml of EtOAc. The organic layer was separated, dried over $MgSO_4$, filtrated and concentrated under reduce pressure. Then, the slightly yellow oil obtained was dissolved in THF (0.5 ml) and added to a suspension of NaH in THF (0.5 ml). The reaction took a pink color and stirred for 24 hours at room temperature. The reaction was quenched by adding 2 ml of water and was extracted with EtOAc (3×5 ml). Combined organic layers were washed with brine (5 ml), dried over $MgSO_4$, filtrated and concentrated under reduce vacuum. The oily residue obtained was purified by flash column chromatography on silica gel using 1 to 10% EtOAc/hexanes to afford a colorless oil in 53% over the 2 steps. $^1H$ NMR (500 MHz, $CDCl_3$): δ 7.35-7.28 (m, 2H), 7.28-7.19 (m, 3H), 7.17-7.07 (m, 2H), 7.03-6.95 (m, 2H), 4.45 (dt, J=12.3, 3.6 Hz, 1H), 3.70 (td, J=12.3, 1.7 Hz, 1H), 3.33 (dd, J=13.8, 11.9 Hz, 1H), 2.84-2.73 (m, 2H), 2.28 (dtd, J=15.2, 11.7, 3.6 Hz, 1H), 2.04 (dtt, J=14.3, 3.5, 1.8 Hz, 1H); $^{13}C$ NMR (125 MHz, $CDCl_3$): δ 160.4, 147.2, 133.9, 130.8, 128.7, 127.7, 126.68, 126.4, 123.7, 121.2, 72.6, 44.0, 41.8, 40.8 ppm. IR (film) 3061, 3026, 2931, 2905, 2871, 1602, 1580, 1490, 1451, 1253, 1226, 1187, 1062, 1050, 757, 700 $cm^{-1}$; LRMS (EI): Mass calcd for $C_{16}H_{16}O$ $[M]^+$, 224.1. found 224.1.

Into a solution of the 2-oxooxepine 3a (0.59 mmol, 1 equiv.) in MeOH (4 ml), one drop of concentrated $H_2SO_4$ was added. Then the solution was sealed and heated at 75 for 1 h 30 min. After that, it was allowed to cool down to room temperature and was neutralized with aqueous saturated $NaHCO_3$ (5 ml). The blurry solution was extracted with EtOAc (3×25 ml). Combined organic layers were dried over $MgSO_4$, filtrated and concentrated under reduce pressure. Purification of the residue obtained by flash column chromatography on silica gel using hexanes/EtOAc 1% to 5%, afforded the ester as a colorless oil in 74% yield (118 mg). $^1H$ NMR (500 MHz, $CDCl_3$): δ=7.29-7.23 (m, 2H), 7.12-7.04 (m, 3H), 6.86 (d, J=7.1, 1H), 6.72-6.62 (m, 3H), 3.68 (s, 3H), 3.34-3.26 (m, 1H), 3.13 (dd, J=13.9, 4.9 Hz, 1H), 2.84-2.65 (m, 3H); $^{13}C$ NMR (125 MHz, $CDCl_3$): δ 174.9, 154.7, 143.2, 131.1, 128.5, 127.9, 127.5, 126.8, 125.0, 119.9, 116.1, 52.2, 42.3, 39.3, 37.4 $cm^{-1}$.

Into a −20° C. brine-ice bath solution of the ester (0.26 mmol, 1 equiv.) in $CH_2Cl_2$ (1 ml) under positive $N_2$ atmosphere, $Et_3N$ (0.39 mmol, 1.5 equiv.) was added dropwise followed by $Tf_2O$ (0.28 mmol, 1.1 equiv.). The reaction was warm up slowly for 1.5 h before it was quenched by dilution with 3 ml of water and extracted with $CH_2Cl_2$ (3×10 ml). Combined organic layers were dried over $MgSO_4$, filtrated and concentrated under reduce pressure. Purification of the residue obtained by flash column chromatography on silica gel using hexanes/EtOAc 1% to 5%, afforded the triflate as a colorless oil in 99% yield (103 mg). $^1H$ NMR (500 MHz, $CDCl_3$): δ 7.31-7.20 (m, 6H), 7.15 (m, 3H), 3.57 (s, 3H), 3.55-3.47 (m, 2H), 3.10 (dd, J=14.1, 7.2 Hz, 1H), 3.02 (dd, J=14.0, 8.3 Hz, 1H), 2.77-2.65 (m, 2H); $^{13}C$ NMR (125 MHz, $CDCl_3$): δ 172.2, 148.2, 142.4, 132.1, 128.5, 128.3, 128.1, 127.3, 126.9, 121.2, 51.6, 42.5, 40.1, 37.0 ppm.

A solution of $Cs_2CO_3$ (0.67 mmol, 3 equiv.), $Pd(OAc)_2$ (0.022 mmol, 0.1 equiv.), BINAP (0.056 mmol, 0.25 equiv.), N,N-dimethylethyldiamine (1.79 mmol, 8.0 equiv.), and the triflate (0.224 mmol, 1.0 equiv.) in THF (1.5 ml) placed in a 2.5 ml microwave biotage vial sealed with a cap, was heated at 140° C. for 25 min. After the reaction achieved room temperature, it was filtrated through a pad of $SiO_2$ using a mixture of $CH_2Cl_2$ and MeOH 15% basified with $Et_3N$ and concentrated under reduced pressure. Purification of the brownish oil through flash column chromatography on silica gel using $CH_2Cl_2$/MeOH 1% to 10% basified with $Et_3N$ afforded the diamine as a greenish oil (m=69 mg, 91% yield). $^1H$ NMR (500 MHz, $CDCl_3$): δ 7.22-7.17 (m, 2H), 7.15-7.09 (m, 3H), 7.03 (tt, J=8.5, 4.2 Hz, 1H), 6.68 (dt, J=7.3, 1.3 Hz, 1H), 6.52 (d, J=8 Hz, 1H), 6.48 (td, J=7.3, 0.8 Hz, 1H), 3.47 (s, 3H), 3.39-3.30 (m, 1H), 3.15 (t, J=6.1 Hz, 2H), 2.80-2.56 (m, 6H), 2.31 (s, 6H); $^{13}C$ NMR (125 MHz, $CDCl_3$): δ 173.3, 146.3, 144.1, 130.8, 128.4, 127.7, 127.3, 126.6, 123.6, 116.5, 110.3, 57.8, 51.6, 45.0, 41.0, 40.6, 39.6, 39.5 ppm. LRMS (EI): Mass calcd for $[C_{21}H_{29}N_2O_2]^+$ $[M+H]^+$, 341.2. found 341.4.

1-(2-(dimethylamino)ethyl)-4-phenyl-4,5-dihydro-H-benzo[b]azepin-2(3H)-one (8)

Into a cold ice bath solution of the diamine (0.117 mmol, 1 equiv) in 3 ml of THF, $LiOH·H_2O$ (0.323 mmol, 5 equiv) was added solved in 1.2 ml of $H_2O$. Then the solution was stirred at 21° C. for 16 h. The reaction was monitored by TLC analysis and confirmed by UPLC. The reaction was buffered with aqueous saturated $NaHCO_3$ solution and extracted 3× with EtOAc (10 ml). Combined organic layers were dried over $Na_2SO_4$, filtrated and concentrated under reduce pressure. The brownish oil obtained was solved in 2 ml of DMF and HBTU (0.117 mmol, 1 equiv) was added followed by Hunig's base (0.117 mmol, 1 equiv). The reaction was monitorized by UPLC. After 16 h the reaction was quenched adding $NaHCO_3$ solution and extracted 3× with EtOAc (10 ml). Combined organic layers were dried over $Na_2SO_4$, filtrated and concentrated under reduce pressure. The crude was the purified through flash column chromatography on silica gel using $CH_2Cl_2$/MeOH 1% to 20% basified with $Et_3N$ to afford the fraction with the tertiary amine. This fraction was concentrated under reduced pressure and treated with HCl saturated solution in ether. The solution was concentrated and recrystallized in EtOAc ether to afford of a white crystalline solid (26 mg, 64%). Mp: 231-233° C.; $^1H$ NMR (500 MHz, $D_3COD$): δ 7.50-7.48 (m, 3H), 7.35-7.27 (m, 4H), 7.23-7.20 (m, 2H), 4.93 (s, 1H), 4.35-4.26 (m, 2H), 3.65 (s, 1H), 3.52 (s, 2H), 3.34-3.32 (m, 1H), 3.01 (s, 6H), 2.86 (s, 1H), 2.58 (s, 1H); $^{13}C$ NMR (126 MHz, $D_3COD$) δ 177.8, 148.1, 145.4, 132.2, 132.1, 131.4, 130.9, 130.6, 126.6, 59.5, 47.7, 46.7, 46.5, 43.0, 42.8. IR (film) 3543, 3029, 2978, 1674, 1668, 1600, 1582, 1434, 1361, 1304, 1282, 1150, 980, 775, 729, 704 $cm^{-1}$. LRMS (EI): Mass calcd for the free base $[C_{20}H_{25}N_2O]^+$ $[M+H]^+$, 309.2. found 309.3.

X-Ray Crystallography Data
Structure Determination of 3f.

The absolute stereochemistry of 3f was determined by the X-ray diffraction. Recrystallized from EtOAc:hexanes. X-ray crystal structure of (R)-4-(4-bromophenyl)-4,5-dihydrobenzo[b]oxepin-2(3H)-one: X-ray diffraction was performed at 100 K and raw frame data were processed using SAINT. Molecular structures was solved using direct methods and refined on F2 by full-matrix least-square techniques. The GOF=1.015 for 172 variables refined to R1=0.0333 for 1939 reflections with I>2α(I). A multi-scan absorption correction was performed and the Flack parameter was 0.01(3). Further information can be found in the CIF file. This crystal was deposited in the Cambridge Crystallographic Data Centre and assigned as CCDC 937893.

Structure Determination of 3m.

The absolute stereochemistry of 3m was determined by the X-ray diffraction. Recrystallized from EtOAc:hexanes. X-ray crystal structure of (4S,5R)-5-methyl-4-phenyl-4,5-dihydrobenzo[b]oxepin-2(3H)-one: X-ray diffraction was performed at 100 K and raw frame data were processed using SAINT. Molecular structures was solved using direct methods and refined on F2 by full-matrix least-square techniques. The GOF=1.233 for 173 variables refined to R1=0.0218 for 2179 reflections with I>2α(I). A multi-scan absorption correction was performed and the Flack parameter was −0.01(19). Further information can be found in the CIF file. This crystal was deposited in the Cambridge Crystallographic Data Centre and assigned as CCDC 939181.

The absolute stereochemistry of 6 was determined by the X-ray diffraction. Recrystallized from EtOAc:hexanes. X-ray crystal structure of (S)-3-methylchroman-2-one: X-ray diffraction was performed at 100 K and raw frame data were processed using SAINT. Molecular structures was solved using direct methods and refined on F2 by full-matrix least-square techniques. The GOF=1.099 for 110 variables refined to R1=0.0244 for 1311 reflections with I>2α(I). A multi-scan absorption correction was performed and the Flack parameter was 0.07(10). Further information can be found in the CIF file. This crystal was deposited in the Cambridge Crystallographic Data Centre and assigned as CCDC 937894.

Structure Determination 8.HCl.

The structure of 8 was determined by the X-ray diffraction. Recrystallized from EtOAc:ether. X-ray crystal structure of N,N-dimethyl-2-(2-oxo-4-phenyl-2,3,4,5-tetrahydro-1H-benzo[b]azepin-1-yl)ethanaminium chloride: X-ray diffraction was performed at 100 K and raw frame data were processed using SAINT. Molecular structures was solved using direct methods and refined on F2 by full-matrix least-square techniques. The GOF=1.042 for 219 variables refined to R1=0.0276 for 3070 reflections with I>2α(I). Further information can be found in the CIF file. This crystal was deposited in the Cambridge Crystallographic Data Centre and assigned as CCDC 945180.

Structure Determination of Azolium C.

The absolute stereochemistry of triazolium salt C was determined by the X-ray diffraction. Recrystallized from EtOAc and ether. X-ray crystal structure of (5aR,10bS)-2-(2,6-diethylphenyl)-4,5a,6,10b-tetrahydroindeno[2,1-b][1,2,4]triazolo[4,3-d][1,4]oxazin-2-ium tetrafluoroborate. X-ray diffraction was performed at 100 K and raw frame data were processed using SAINT. Molecular structures was solved using direct methods and refined on F2 by full-matrix least-square techniques. The GOF=1.022 for 293 variables refined to R1=0.0247 for 3142 reflections with I>2α(I). A multi-scan absorption correction was performed and the Flack parameter was −0.06(10). Further information can be found in the CIF file. This crystal was deposited in the Cambridge Crystallographic Data Centre and assigned as CCDC 937900.

REFERENCES

1. Jacobsen, E. N et al. *Comprehensive Asymmetric Catalysis. I-III;* 1-3 ed.; Springer: Berlin, Germany, 1999.
2. (a) Denmark, S. E. et al. *Angew. Chem. Int. Ed* 2008, 47, 1560-1638. (b) Denmark, S. E.; et al. *Acc. Chem. Res.* 2000, 33, 432-440.
3. Yamamoto, H. *Lewis acids in organic synthesis*; Wiley-VCH: Weinheim; New York, 2000.
4. (a) MacMillan, D. W. C. *Nature* 2008, 455, 304-308. (b) Mukherjee, S.; et al. *Chem. Rev.* 2007, 107, 5471-5569.
5. (a) Doyle, A. G. et al. *Chem. Rev.* 2007, 107, 5713-5743. (b) Pihko, P. M. *Angew. Chem. Int. Ed.* 2004, 43, 2062-2064. (c) Taylor, M. S. et al. N. *Angew. Chem. Int. Ed.* 2006, 45, 1520-1543. (d) Jain, P.; et al. *J. Am. Chem. Soc.* 2010, 132, 11884-11886. (e) Liang, T. et al. *Angew. Chem. Int. Ed.* 2010, 49, 9734-9736. (f) Rueping, M. et al. *Angew. Chem. Int. Ed.* 2011, 50, 6706-6720. (g) Akiyama, T. *Chem. Rev.* 2007, 107, 5744-5758. (h) Shen, B. et al. *Nature* 2010, 465, 1027-U1082. (i) Terada, M. *Synthesis* 2010, 1929-1982.
6. For leading reviews, see: (a) Lyons, T. W. et al. *Chem. Rev.* 2010, 110, 1147-1169. (b) Engle, K. M.; et al. *Acc. Chem. Res.* 2011, 45, 788-802.
7. Hartwig, J. F. *Organotransition Metal Chemistry*; University Science Books: Mill Valley, C A, 2010.
8. For reviews and recent examples on NHC catalysis covering these different reaction manifolds, see: (a) Enders, D. et al. *Chem. Rev.* 2007, 107, 5606-5655. (b) Marion, N. et al. *Angew. Chem. Int. Ed* 2007, 46, 2988-3000. (c) Phillips, E. M. et al. A. *Aldrichimica Acta* 2009, 43, 55-66. (d) Ryan, S. J. et al. *Chem. Soc. Rev.* 2013, 42, 4906-4917. (e) Hao, L. et al. *Org. Lett.* 2012, 14, 2154-2157. (f) Jian, T. Y. et al. *Chem. Commun.* 2012, 48, 10907-10909. (g) Jian, T. Y. et al. *Org. Biomol. Chem.* 2013, 11, 158-163. (h) Nair, V. et al. *Chem. Soc. Rev.* 2011, 40, 5336-5346. (i) Vora, H. U. et al. *Adv. Synth. Catal.* 2012, 354, 1617-1639. (j) Douglas, J. et al. *Synthesis* 2012, 2295-2309. (k) Izquierdo, J. et al. *Angew. Chem. Int. Ed.* 2012, 51, 11686-11698. (l) De Sarkar, S. et al. *Chem. Eur. J.* 2013, 19, 4664-4678.
9. (a) Sheehan, J. C. et al. *J. Am. Chem. Soc.* 1966, 88, 3666-3667. (b) Enders, D. et al. *Helv. Chim. Acta* 1996, 79, 1899-1902. (c) Breslow, R. *J. Am. Chem. Soc.* 1958, 80, 3719-3726. (d) Enders, D. et al. *Helv. Chim. Acta* 1996, 79, 1217-1221. (e) Stetter, H. *Angew. Chem. Int. Ed.* 1976, 15, 639-712. (f) Stetter, H. et al. *Chem. Ber.* 1979, 112, 84-94.
10. (a) Burstein, C. et al. *Chem. Int. Ed.* 2004, 43, 6205-6208. (b) Sohn, S. S. et al. *J. Am. Chem. Soc.* 2004, 126, 14370-14371. (c) Chan, A. et al. *Org. Lett.* 2005, 7, 905-908.
11. (a) Cohen, D. T. et al. *Angew. Chem. Int. Ed.* 2011, 50, 1678-1682. (b) Cohen, D. T. et al. *Chem. Sci.* 2012, 3, 53-57. (c) Dugal-Tessier, J. et al *Angew. Chem. Int. Ed* 2012, 51, 4963-4967. (d) Cardinal-David, B. et al. *J. Am. Chem. Soc.* 2010, 132, 5345-5346. (e) Raup, D. E. A. et al. *Nat. Chem.* 2010, 2, 766-771.
12. (a) Mo, J. M. et al. *J. Am. Chem. Soc.* 2012, 134, 8810-8813. (b) Rong, Z. Q. et al. *Org. Lett.* 2011, 13, 4080-4083. (c) Qi, J. et al. *Chem. Eur. J.* 2013, 19, 4146-4150.
13. Zhao, X. D. et al. *J. Am. Chem. Soc.* 2011, 133, 12466-12469.
14. (a) Mattson, A. E. et al. *J. Am. Chem. Soc.* 2007, 129, 4508-4509. (b) Li, T. H. et al. *J. Am. Chem. Soc.* 1991, 113, 7771-7773. (c) Pande, P. et al. *J. Am. Chem. Soc.* 1999, 121, 6773-6779. (d) Veldhuyzen, W. F. et al. *J. Am. Chem. Soc.* 2003, 125, 14005-14013. (e) Weinert, E. E. et al. *J. Am. Chem. Soc.* 2006, 128, 11940-11947.
15. (a) Wan, P. et al. *Can. J. Chem.* 1996, 74, 465-475. (b) Chiang, Y. et al. *Pure Appl. Chem.* 2000, 72, 2299-2308. (c) Van de Water, R. W. et al. *Tetrahedron* 2002, 58, 5367-5405. (d) Luan, Y. et al. *J. Am. Chem. Soc.* 2012, 134, 19965-19968. (e) Willis, N. J. et al. *Chem. Eur. J.* 2012, 18, 9160-9173. (f) Pathak, T. P. et al. *J. Am. Chem. Soc.* 2010, 132, 7870-7871.
16. During review of this work, a related reaction involving the NHC-catalyzed addition of homoenolate equivalents to stable o-QMs was reported by Ye and coworkers: DOI: 10.1002/anie.201303903.
17. Additional fluoride sources were examined, including Me4N.F and TBAT, but these only provided trace amounts of desired product. See Supporting information for details.
18. The avoidance of standard nucleophilic amine bases used for NHC production from the corresponding azolium salt (e.g., triazabicyclodecene, 8-diazabicyclo[5.4.0]undec-7-ene, Et3N) was key for a successful process and understandable given the highly reactive nature of the o-QM in solution during the reaction. Lastly, omitting the CsF in the reaction based on entry 9, Table 1, FIG. 2, provides no observable product.
19. Cronotonaldehyde as a substrate gave prodominantly the formal [4+2] product in a 57:43 ratio of formal [4+3] to [4+2] products (overall yield of 48%). The er for the [4+3] adduct was 95:5 and the er for the [4+2] compound was 99:1. Investigations to change this ratio by modulation of the reaction conditions (e.g., base, solvent) have resulted in no improvement to date.
20. (a) Kawanaka, Y. et al. *J. Am. Chem. Soc.* 2009, 131, 18028-18029. (b) Phillips, E. M. et al. *Org. Lett.* 2009, 11, 105-108.
21. For the NHC-catalyzed addition of ketene-derived enolates to stable o-quinone methides, see: Lv, H. et al. *Adv. Syn. Catal.* 2009, 351, 2882-2826
22. Macias, F. A.; Varela, R. M.; Torres, A.; Molinillo, J. M. G. *J. Nat. Prod.* 1999, 62, 1636-1639.
23. Porter, J. H. et al. *Psychopharmacol.* 2009, 203, 189-191.
24. (a) Costantino, L. et al. *Curr. Med Chem.* 2006, 13, 65-85. (b) Schuetz, H. *Benzodiazepines II. A Handbook*; Springer Verlag: Berlin, 1989.
25. (a) Das, J. et al. *J. Med. Chem.* 1992, 35, 2610-2617. (b) Das, J. et al. *J. Med Chem.* 1992, 35, 773-780. (c) Floyd, D. M. et al. *J. Med. Chem.* 1992, 35, 756-772. (d) Floyd, D. M. et al. *J. Org. Chem.* 1990, 55, 5572-5579.
26. O'Connor, S. E. et al. *Fund. & Clin. Pharmacol.* 1999, 13, 145-153.
27. Grover, G. J. et al. *J. Cardiovasc. Pharmacol.* 1990, 16, 219-227.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:
1. A compound having a formula:

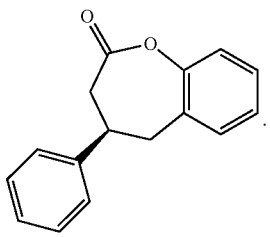 [SMILES: O=C1C[C@H](c2ccccc2)Cc2ccccc2O1]

2. A method for preparing the compound of claim 1, the method comprising:
(a) reacting a compound having the formula
(i)

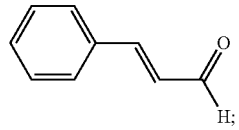

and
(ii) an N-heterocyclic carbene (NHC) to produce an NHC-homoenolate;
(b) reacting a compound having the formula
(iii)

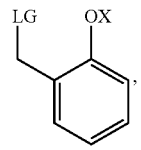

wherein:
LG is a leaving group; and
X is a protecting group; and
(iv) a source of F⁻ to produce an o-quinone methide; and
(c) reacting the NHC-homoenolate of reaction (a) and the o-quinone methide of reaction (b) to produce the compound of claim 1.
3. The method of claim 2, wherein the NHC is selected from a group of compounds or salts thereof having a formula:

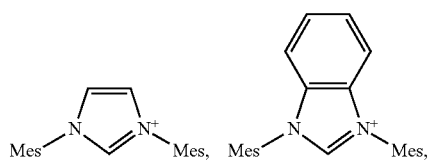

-continued
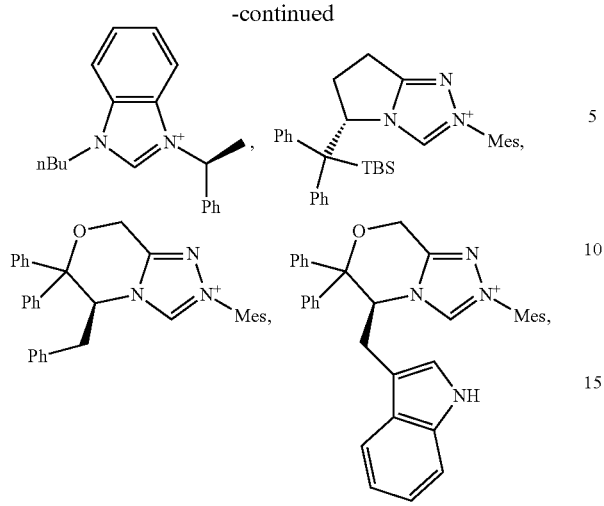
-continued
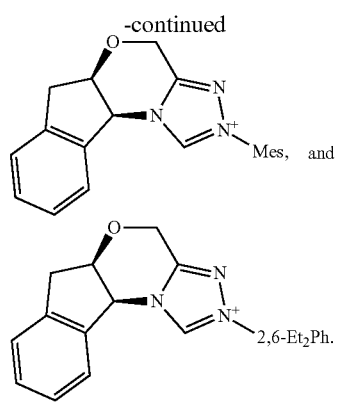
4. The method of claim 2, wherein LG is Br⁻, Cl⁻, or a sulfonate ester.
* * * * *